(12) United States Patent
Marcoux et al.

(10) Patent No.: US 10,633,354 B2
(45) Date of Patent: Apr. 28, 2020

(54) SUBSTITUTED TRICYCLIC HETEROCYCLIC COMPOUNDS

(71) Applicant: BRISTOL-MYERS SQUIBB COMPANY, Princeton, NJ (US)

(72) Inventors: David Marcoux, Pennington, NJ (US); Hai-Yun Xiao, Belle Mead, NJ (US); T. G. Murali Dhar, Newton, PA (US); Alaric J. Dyckman, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/329,399

(22) PCT Filed: Aug. 31, 2017

(86) PCT No.: PCT/US2017/049572
§ 371 (c)(1),
(2) Date: Feb. 28, 2019

(87) PCT Pub. No.: WO2018/045149
PCT Pub. Date: Mar. 8, 2018

(65) Prior Publication Data
US 2019/0218193 A1 Jul. 18, 2019

Related U.S. Application Data

(60) Provisional application No. 62/382,962, filed on Sep. 2, 2016.

(51) Int. Cl.
*C07D 277/60* (2006.01)
*C07D 277/84* (2006.01)
(Continued)

(52) U.S. Cl.
CPC ......... *C07D 277/84* (2013.01); *C07D 261/20* (2013.01); *C07D 277/60* (2013.01);
(Continued)

(58) Field of Classification Search
CPC .. C07D 277/60; C07D 277/84; C07D 261/20; C07D 333/50; C07D 333/74; C07D 417/04
See application file for complete search history.

(56) References Cited

U.S. PATENT DOCUMENTS 3,843,666 A 10/1974 Coombs et al.
5,670,522 A 9/1997 Lesson et al.
(Continued)

FOREIGN PATENT DOCUMENTS

EP 223914 A1 9/2010
EP 2592071 A1 5/2013
(Continued)

OTHER PUBLICATIONS

Dinges, et al., "1,4-Dihydroindeno[1,2-c]pyrazoles with Acetylenic Side Chains as Novel and Potent Multitargeted Receptor Tyrosine Kinase Inhibitors with Low Affinity for the hERG Ion Channel", J. Med. Chem., 2007, vol. 50, pp. 2011-2029.
(Continued)

*Primary Examiner* — Laura L Stockton
(74) *Attorney, Agent, or Firm* — Gary Greenblatt

(57) ABSTRACT

Disclosed are compounds of Formula (I), Formula (II), Formula (III), and Formula (IV) or salts thereof, wherein $R_2$ is —OH or —OP(O)(OH)$_2$; and $R_1$ is defined herein. Also disclosed are methods of using such compounds as selective agonists for G protein coupled receptor S1P$_1$, and pharmaceutical compositions comprising such compounds. These compounds are useful in treating, preventing, or slowing the progression of diseases or disorders in a variety of therapeutic areas, such as autoimmune diseases and vascular disease.

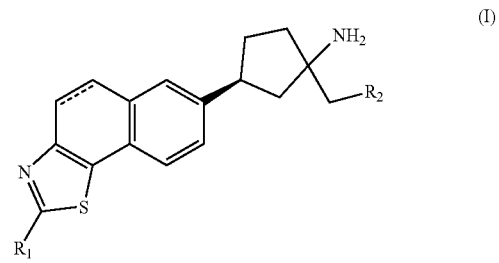

(I)

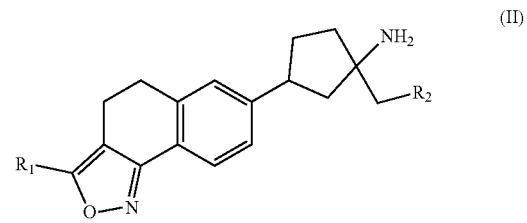

(II)

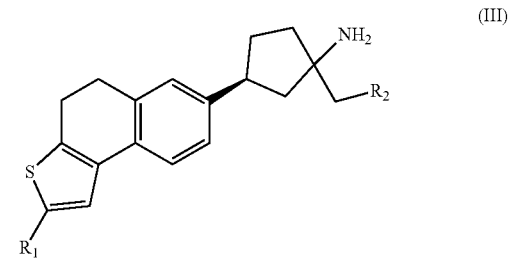

(III)

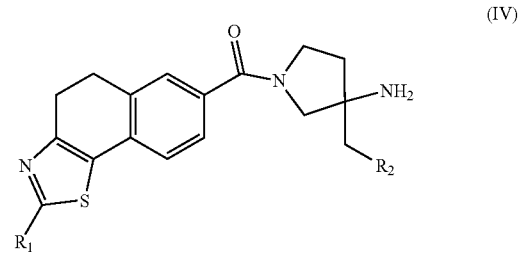

(IV)

7 Claims, No Drawings

(51) Int. Cl.

| | | |
|---|---|---|
| C07D 261/20 | (2006.01) | |
| C07D 333/50 | (2006.01) | |
| C07D 333/74 | (2006.01) | |
| C07D 417/04 | (2006.01) | |
| C07F 9/6553 | (2006.01) | |
| C07F 9/6541 | (2006.01) | |
| C07F 9/653 | (2006.01) | |
| C07D 417/06 | (2006.01) | |
| C07D 417/10 | (2006.01) | |
| C07D 417/14 | (2006.01) | |
| C07F 9/117 | (2006.01) | |

(52) U.S. Cl.
CPC ......... *C07D 333/50* (2013.01); *C07D 333/74* (2013.01); *C07D 417/04* (2013.01); *C07D 417/06* (2013.01); *C07D 417/10* (2013.01); *C07D 417/14* (2013.01); *C07F 9/117* (2013.01); *C07F 9/6541* (2013.01); *C07F 9/65324* (2013.01); *C07F 9/655354* (2013.01)

(56) References Cited

U.S. PATENT DOCUMENTS

| | | | |
|---|---|---|---|
| 6,251,922 B1 | 6/2001 | Jahne et al. | |
| 7,115,545 B1 | 10/2006 | Witschel et al. | |
| 9,216,972 B2 * | 12/2015 | Dhar ............ | C07D 231/54 |
| 2004/0259904 A1 | 12/2004 | Tong et al. | |
| 2005/0027125 A1 | 2/2005 | Linden et al. | |
| 2007/0281963 A1 | 12/2007 | Fukumoto et al. | |

FOREIGN PATENT DOCUMENTS

| | | |
|---|---|---|
| GB | 1354097 | 5/1974 |
| GB | 1354098 | 5/1974 |
| JP | 4899161 | 4/1972 |
| JP | 47016454 | 9/1972 |
| JP | 47022226 | 10/1972 |
| JP | 2004-18489 | 1/2004 |
| WO | WO199725317 A1 | 7/1997 |
| WO | WO199813356 A1 | 4/1998 |
| WO | WO199917769 A1 | 4/1999 |
| WO | WO200027822 A2 | 5/2000 |
| WO | WO200187846 A2 | 11/2001 |
| WO | WO2003061655 A1 | 7/2003 |
| WO | WO2003097609 A1 | 11/2003 |
| WO | WO2003105840 A2 | 12/2003 |
| WO | WO2005095387 A1 | 10/2005 |
| WO | WO2006052555 A2 | 5/2006 |
| WO | WO2008028168 A2 | 3/2008 |
| WO | WO2008039520 A2 | 4/2008 |
| WO | WO2008053300 A1 | 5/2008 |
| WO | WO2008094896 A1 | 8/2008 |
| WO | WO2008118790 A1 | 10/2008 |
| WO | WO2009078983 A1 | 6/2009 |
| WO | WO2009089305 A1 | 7/2009 |
| WO | WO2009123971 A1 | 10/2009 |
| WO | WO2010011316 A1 | 1/2010 |

OTHER PUBLICATIONS

Ho, et al. "(6,7-Dimethoxy-2,4-dihydroindeno[1,2-c]pyrazol-3-yl)phenylamines: Platelet-Derived Growth Factor Receptor Tyrosine Kinase Inhibitors with Broad Antiproliferative Activity against Tumor Cells", J. Med. Chem., 2005, vol. 48, pp. 8163-8173.

International Preliminary Report on Patentability, PCT/US2017/049572, dated Mar. 5, 2019.

Kumar, et al., "Efficient Routes to Pyrazolo[3,4-b]indoles and Pyrazolo[1,5-a]benzimidazoles via Palladium- and Copper-Catalyzed Intramolecular C_C and C—N Bond Formation", J. Org. Chem., 2009, vol. 74, pp. 7046-7051.

Marcoux, et al., "Identification of potent tricyclic prodrug S1P1 receptor modulators", MedChemComm, 2017, vol. 8, pp. 725.

Ponomarev, et al., "Nature of the excited states of dialklamino derivatives of aromatic and heteroaromatic compounds with annelated oxazole rings", Teoreticheskaya i Eksperimental'naya Khimiya, 1990, 26 (6), pp. 644-650.

Ponomarev, et al., "Spin-orbit interaction of the $\pi$ $\pi$*-states in molecules with annelated oxazole rings", Teoreticheskaya i Eksperimental'naya Khimiya, 1990, vol. 26 (4), pp. 403-406.

Rosen, et al., "Discovery of the first known small-molecule inhibitors of heme-regulated eukaryotic initiation factor $2\alpha$ (HRI) kinase", Bioorganic & Medicinal Chemistry Letters, 2009, vol. 19, pp. 6548-6551.

Shen, et al.,, "Discovery of Novel Tricyclic Full Agonists for the G-Protein-Coupled Niacin Receptor 109A with Minimized Flushing in Rats", J. Med. Chem, 2009, vol. 52, pp. 2587-2602.

Tao, et al., "Discovery of 4'-(1,4-dihydro-indeno[1,2-c]pyrazol-3-yl)-benzonitrites and 4'-(1,4-dihydro-indenol[1,2-c] pyrazol-3-yl)-pryridine-2'-carbonitriles as potent checkpoint kinase 1 (Ckh1) inhibitors", Bioorganic & Medicinal Chemistry Letters, 2007, vol. 17, pp. 5944-5951.

\* cited by examiner

SUBSTITUTED TRICYCLIC HETEROCYCLIC COMPOUNDS

This application is a national phase application under 35 U.S.C. § 371 of International Patent Application No. PCT/US2017/049572, filed Aug. 31, 2017, which claims priority to U.S. Provisional Application No. 62/382,962, filed Sep. 2, 2016, which are expressly incorporated fully herein by reference.

DESCRIPTION

The present invention generally relates to substituted tricyclic heterocyclic compounds useful as $S1P_1$ agonists. Provided herein are substituted tricyclic heterocyclic compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

BACKGROUND OF THE INVENTION

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Downregulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function. Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., *Bioorg. Med. Chem. Lett.*, 14:3501 (2004); Sanna et al., *J. Biol. Chem.*, 279:13839 (2004); Anliker et al., *J. Biol. Chem.*, 279:20555 (2004); Mandala et al., *J. Pharmacol. Exp. Ther.*, 309:758 (2004).)

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., *J. Biol. Chem.*, 277:21453 (2002); Mandala et al., *Science*, 296:346 (2002); Fujino et al., *J. Pharmacol. Exp. Ther.*, 305:45658 (2003); Brinkman et al., *Am. J. Transplant*, 4:1019 (2004); Webb et al., *J. Neuroimmunol.*, 153:108 (2004); Morris et al., *Eur. J. Immunol.*, 35:3570 (2005); Chiba, *Pharmacology & Therapeutics*, 108:308 (2005); Kahan et al., *Transplantation*, 76:1079 (2003); and Kappos et al., *N. Engl. J. Med.*, 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the SW family of receptors that is largely responsible for the pharmacological effects of FTY720 in animals and humans.

Clinical studies have demonstrated that treatment with FTY720 results in bradycardia in the first 24 hours of treatment (Kappos et al., *N. Engl. J. Med.*, 335:1124 (2006)). The observed bradycardia is commonly thought to be due to agonism at the $S1P_3$ receptor. This conclusion is based on a number of cell based and animal experiments.

These include the use of $S1P_3$ knockout animals which, unlike wild type mice, do not demonstrate bradycardia following FTY720 administration and the use of $S1P_1$ selective compounds. (Hale et al., *Bioorg. Med. Chem. Lett.*, 14:3501 (2004); Sanna et al., *J. Biol. Chem.*, 279:13839 (2004); and Koyrakh et al., *Am. J. Transplant.*, 5:529 (2005)).

The following applications have described compounds as $S1P_1$ agonists: WO 03/061567 (U.S. Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Publication No. 2007/0203100), WO 06/047195, WO 06/100633, WO 06/115188, WO 06/131336, WO 2007/024922, WO 07/109330, WO 07/116866, WO 08/023783 (U.S. Publication No. 2008/0200535), WO 08/029370, WO 08/114157, WO 08/074820, WO 09/043889, WO 09/057079, WO 2014/130752, WO 2016/028959, and U.S. Pat. No. 6,069,143. Also see Hale et al., *J. Med. Chem.*, 47:6662 (2004).

There still remains a need for compounds useful as $S1P_1$ agonists and yet having selectivity over $S1P_3$.

Applicants have found potent compounds that have activity as $S1P_1$ agonists. Further, applicants have found compounds that have activity as $S1P_1$ agonists and are selective over $S1P_3$. These compounds are provided to be useful as pharmaceuticals with desirable stability, bioavailability, therapeutic index, and toxicity values that are important to their drugability.

SUMMARY OF THE INVENTION

The present invention provides substituted tricyclic heterocyclic compounds of Formula (I), Formula (II), Formula (III), or Formula (IV), which are useful as modulators of $S1P_1$ activity, including salts thereof.

The present invention also provides pharmaceutical compositions comprising a compound of Formula (I), Formula (II), Formula (III), or Formula (IV) and/or a pharmaceutically acceptable salt thereof; and a pharmaceutically acceptable carrier.

The present invention also provides a method of treating a disease or disorder associated with the activity of G protein-coupled receptor $S1P_1$, the method comprising administering to a mammalian patient a compound of Formula (I), Formula (II), Formula (III), or Formula (IV) and/or a pharmaceutically acceptable salt thereof.

The present invention also provides processes and intermediates for making the compounds of Formula (I), Formula (II), Formula (III), or Formula (IV) and/or salts thereof.

The present invention also provides a compound of Formula (I), Formula (II), Formula (III), or Formula (IV) and/or a pharmaceutically acceptable salt thereof, for use in therapy.

The present invention also provides the use of the compounds of Formula (I), Formula (II), Formula (III), or Formula (IV) and/or pharmaceutically acceptable salts thereof, for the manufacture of a medicament for the treatment or prophylaxis of $S1P_1$ receptor-related conditions, such as autoimmune and vascular diseases.

The compounds of Formula (I), Formula (II), Formula (III), or Formula (IV) and compositions comprising the compounds of Formula (I), Formula (II), Formula (III), or Formula (IV) may be used in treating, preventing, or curing various $S1P_1$ related conditions. Pharmaceutical compositions comprising these compounds are useful in treating, preventing, or slowing the progression of diseases or disorders in a variety of therapeutic areas, such as autoimmune and vascular diseases.

These and other features of the invention will be set forth in expanded form as the disclosure continues.

DETAILED DESCRIPTION

The first aspect of the present invention provides at least one compound of Formula (I):

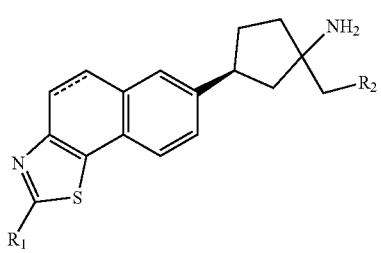

or a salt thereof, wherein:
=== represents either a single bond or a double bond;
$R_1$ is —$(CH_2)_{2-3}CH_3$, —$(CH_2)_{5-6}CH_3$, —$(CH_2)_{1-2}C(CH_3)_3$, —$NR_a(CH_2)_3CH_3$, —$O(CH_2)_{3-5}CH_3$, —$S(CH_2)_{3-4}CH_3$, —$OCH_2CH_2O(CH_2)_3CH_3$, methylphenyl, or methoxyphenyl;
$R_2$ is —OH or —$OP(O)(OH)_2$; and
$R_a$ is H or —$CH_3$.

The second aspect of the present invention provides at least one compound of Formula (II):

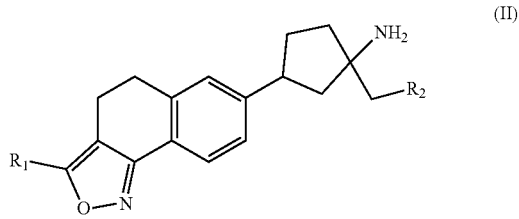

or a salt thereof, wherein:
$R_1$ is —$(CH_2)_5CH_3$ or

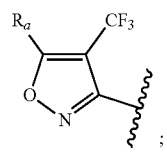

$R_a$ is —$(CH_2)_5CH_3$; and
$R_2$ is —OH or —$OP(O)(OH)_2$.

The third aspect of the present invention provides at least one compound of Formula (III):

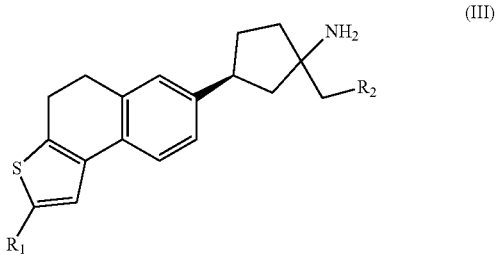

or a salt thereof, wherein:
$R_1$ is —$(CH_2)_4CH_3$; and
$R_2$ is —OH or —$OP(O)(OH)_2$.

The fourth aspect of the present invention provides at least one compound of Formula (IV):

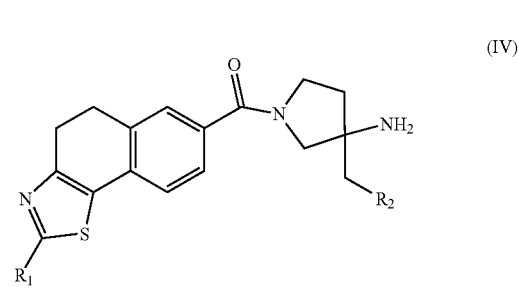

or a salt thereof, wherein:
R₁ is —(CH₂)₄CH₃ or -isoxazolyl substituted with —CF₃ and phenyl; and
R₂ is —OH or —OP(O)(OH)₂.

One embodiment provides a compound of Formula (I) or a salt thereof, wherein === represents a single bond. Compounds of this embodiment have the structure of Formula (Ia):

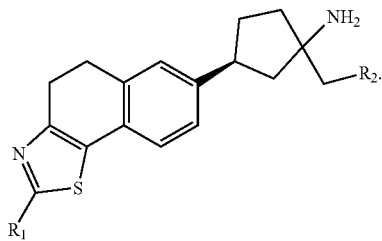

(Ia)

One embodiment provides a compound of Formula (I) or a salt thereof, wherein === represents a double bond. Compounds of this embodiment have the structure of Formula (Ib):

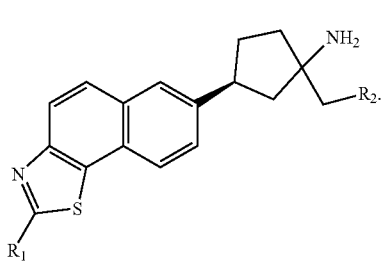

(Ib)

One embodiment provides a compound of Formula (I) or a salt thereof, wherein R₁ is —(CH₂)₂₋₃CH₃, —(CH₂)₅₋₆CH₃, or —(CH₂)₁₋₂C(CH₃)₃; and R₂ is —OH or —OP(O)(OH)₂.

One embodiment provides a compound of Formula (I) or a salt thereof, wherein R₁ is —NR_a(CH₂)₃CH₃, —O(CH₂)₃₋₅CH₃, —S(CH₂)₃₋₄CH₃, or —OCH₂CH₂O(CH₂)₃CH₃; R₂ is —OH or —OP(O)(OH)₂; and R_a is H or —CH₃.

One embodiment provides a compound of Formula (I) or a salt thereof, wherein: R₁ is methylphenyl or methoxyphenyl; and R₂ is —OH or —OP(O)(OH)₂.

One embodiment provides a compound of Formula (II) or a salt thereof, wherein: R₁ is —(CH₂)₅CH₃; and R₂ is —OH or —OP(O)(OH)₂.

One embodiment provides a compound of Formula (II) or a salt thereof, wherein: R₁ is

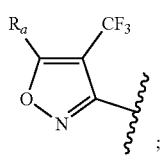

;

R_a is —(CH₂)₅CH₃; and R₂ is —OH or —OP(O)(OH)₂.
One embodiment provides a compound of Formula (IV) or a salt thereof, wherein: R₁ is

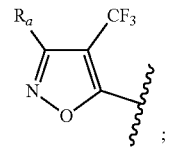

;

R_a is phenyl; and R₂ is —OH or —OP(O)(OH)₂.

One embodiment provides a compound of Formula (IV) or a salt thereof, wherein: R₁ is —(CH₂)₄CH₃; and R₂ is —OH or —OP(O)(OH)₂.

One embodiment provides a compound of Formula (I), Formula (II), or Formula III), or Formula (IV) or a salt thereof, wherein R₂ is —OH.

One embodiment provides a compound of Formula (I), Formula (II), Formula (III), or Formula (IV) or a salt thereof, wherein R₂ is —OP(O)(OH)₂.

One embodiment provides a compound of Formula (I), Formula (II), or Formula (III), or a salt thereof, wherein said compound is selected from: (1R,3S)-1-amino-3-(2-heptyl-4,5-dihydronaphtho[2,1-d]thiazol-7-yl)cyclopentyl) methanol, TFA salt (1); ((1R,3S)-1-amino-3-(2-propyl-4,5-dihydronaphtho[2,1-d]thiazol-7-yl)cyclopentyl) methanol, trifluoroacetic acid salt (2); ((1R,3S)-1-amino-3-(2-(3,3-dimethylbutyl)-4,5-dihydronaphtho[2,1-d]thiazol-7-yl)cyclopentyl)methanol, trifluoroacetic acid salt (3); ((1R,3S)-1-amino-3-(2-neopentyl-4,5-dihydronaphtho[2,1-d]thiazol-7-yl)cyclopentyl) methanol, trifluoroacetic acid salt (4); ((1R,3S)-1-amino-3-(2-hexyl-4,5-dihydronaphtho[2,1-d]thiazol-7-yl)cyclopentyl)methanol, trifluoroacetic acid salt (5); ((1R,3S)-1-amino-3-(2-butyl-4,5-dihydronaphtho[2,1-d]thiazol-7-yl)cyclopentyl)methanol, trifluoroacetic acid salt (6); ((1R,3S)-1-amino-3-(2-(2-butoxyethoxy)-4,5-dihydronaphtho[2,1-d]thiazol-7-yl)cyclopentyl)methanol, trifluoroacetic acid salt (7); ((1R,3S)-1-amino-3-(2-butoxy-4,5-dihydronaphtho[2,1-d]thiazol-7-yl)cyclopentyl)methanol, trifluoroacetic acid salt (8); ((1R,3S)-1-amino-3-(2-(hexyloxy)-4,5-dihydronaphtho[2,1-d]thiazol-7-yl)cyclopentyl) methanol, trifluoroacetic acid salt (9); ((1R,3S)-1-amino-3-(2-(butylthio)-4,5-dihydronaphtho[2,1-d]thiazol-7-yl)cyclopentyl)methanol, trifluoroacetic acid salt (10); ((1R,3S)-1-amino-3-(2-(pentylthio)-4,5-dihydronaphtho[2,1-d]thiazol-7-yl)cyclopentyl) methanol, trifluoroacetic acid salt (11); ((1R,3S)-1-amino-3-(2-(pentyloxy)-4,5-dihydronaphtho[2,1-d]thiazol-7-yl)cyclopentyl)methanol, trifluoroacetic acid salt (12); ((1R,3S)-1-amino-3-(2-(hexyloxy)naphtho[2,1-d]thiazol-7-yl)cyclopentyl)methanol, trifluoroacetic acid salt (13); ((1R,3S)-1-amino-3-(2-(butylthio)naphtho[2,1-d]thiazol-7-yl)cyclopentyl)methanol, trifluoroacetic acid salt (14); ((1R,3S)-1-amino-3-(2-(pentyloxy)naphtho[2,1-d]thiazol-7-yl)cyclopentyl)methanol, trifluoroacetic acid salt (15); ((1R,3S)-1-amino-3-(2-butoxynaphtho[2,1-d]thiazol-7-yl)cyclopentyl)methanol, trifluoroacetic acid salt (16); ((1R,3S)-1-amino-3-(2-(butylamino)-4,5-dihydronaphtho[2,1-d]thiazol-7-yl)cyclopentyl)methanol, trifluoroacetic acid salt (17); ((1R,3S)-1-amino-3-(2-(butyl(methyl)amino)-4,5-dihydronaphtho[2,1-d]thiazol-7-yl)cyclopentyl) methanol, trifluoroacetic acid salt (18); ((1R,3S)-1-amino-3-(2-(p-tolyl)-4,5-dihydronaphtho[2,1-d]thiazol-7-yl)cyclopentyl)methanol, trifluoroacetic acid salt (19); ((1R,3S)-1-amino-3-(2-(3-methoxyphenyl)-4,5-dihydronaphtho[2,1-d]thiazol-7-yl) cyclopentyl)methanol, trifluoroacetic acid salt (20); ((1R,3S)-1-amino-3-(2-pentyl-4,5-dihydronaphtho[2,1-b]thiophen-7-yl)cyclopentyl)methanol, trifluoroacetic acid salt (21); ((1R,3S)-1-amino-3-(2-(hexyloxy)-4,5-dihydronaphtho[2,1-d]thiazol-7-yl)cyclopentyl) methyl dihydrogen phosphate, trifluoroacetic acid salt (30); ((1R,3S)-1-amino-3-(2-(butylthio)-4,5-dihydronaphtho[2,1-d]thiazol-7-yl)cyclopentyl)methyl dihydrogen phosphate, trifluoroacetic acid salt (31); ((1R,3S)-1-amino-3-(2-(butylamino)-4,5-dihydronaphtho[2,1-d]thiazol-7-yl)cyclopentyl)methyl dihydrogen phosphate, trifluoroacetic acid salt (32); ((1R,3S)-1-amino-3-(2-(pentylthio)-4,5-dihydronaphtho[2,1-d]thiazol-7-yl)cyclopentyl)methyl dihydrogen phosphate, trifluoroacetic acid salt (33); ((1R,3S)-1-amino-3-(2-(pentyloxy)-4,5-dihydronaphtho[2,1-d]thiazol-7-yl) cyclopentyl) methyl dihydrogen phosphate, trifluoroacetic acid salt (34); ((1R,3S)-1-amino-3-(2-(p-tolyl)-4,5-dihydronaphtho[2,1-d]thiazol-7-yl)cyclopentyl)methyl dihydrogen phosphate, trifluoroacetic acid salt (35); ((1R,3S)-1-amino-3-(2-(3-methoxyphenyl)-4,5-dihydronaphtho[2,1-d]thiazol-7-yl) cyclopentyl)methyl dihydrogen phosphate, trifluoroacetic acid salt (36); ((1R,3S)-1-amino-3-(2-(3,3-dimethylbutyl)-4,5-dihydronaphtho[2,1-d]thiazol-7-yl)cyclopentyl) methyl dihydrogen phosphate, trifluoroacetic acid salt (37); ((1R,3S)-1-amino-3-(2-neopentyl-4,5-dihydronaphtho[2,1-d]thiazol-7-yl)cyclopentyl)methyl dihydrogen phosphate, trifluoroacetic acid salt (38); ((1R,3S)-1-amino-3-(2-butyl-4,5-dihydronaphtho[2,1-d]thiazol-7-yl)cyclopentyl)methyl dihydrogen phosphate, trifluoroacetic acid salt (39); ((1R,3S)-1-amino-3-(2-hexyl-4,5-dihydronaphtho[2,1-d]thiazol-7-yl)cyclopentyl)methyl dihydrogen phosphate, trifluoroacetic acid salt (40); (1-amino-3-(3-hexyl-4,5-dihydronaphtho[1,2-c]isoxazol-7-yl)cyclopentyl)methyl dihydrogen phosphate (41-45); ((1R,3S)-1-amino-3-(2-butoxynaphtho[2,1-d]thiazol-7-yl)cyclopentyl)methyl dihydrogen phosphate, TFA salt (46); ((1R,3S)-1-amino-3-(2-(hexyloxy)naphtho[2,1-d]thiazol-7-yl)cyclopentyl)methyl dihydrogen phosphate, TFA salt (47); and ((1R,3S)-1-amino-3-(2-(butylthio)naphtho[2,1-d]thiazol-7-yl)cyclopentyl)methyl dihydrogen phosphate (48).

One embodiment provides a compound of Formula (IV) or a salt thereof, wherein said compound is (3-amino-3-(hydroxymethyl)pyrrolidin-1-yl)(2-(3-phenyl-4-(trifluoromethyl)isoxazol-5-yl)-4,5-dihydronaphtho[2,1-d]thiazol-7-yl)methanone (49 and 50); or (3-amino-3-(hydroxymethyl)pyrrolidin-1-yl)(2-(3-phenyl-4-(trifluoromethyl) isoxazol-5-yl)-4,5-dihydronaphtho[2,1-d] thiazol-7-yl)methanone (51 to 53).

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I); or alternatively, two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I), Formula (II), Formula (III), or Formula (IV) can be provided as amorphous solids or crystalline solids. Lyophilization can be employed to provide the compounds of Formula (I), Formula (II), Formula (III), or Formula (IV) as amorphous solids.

It should further be understood that solvates (e.g., hydrates) of the compounds of Formula (I), Formula (II), Formula (III), or Formula (IV) are also within the scope of the present invention. The term "solvate" means a physical association of a compound of Formula (I), Formula (II), Formula (III), or Formula (IV) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), Formula (II), Formula (III), or Formula (IV) subsequent to their preparation, can be isolated and purified to obtain a composition containing an amount by weight equal to or greater than 99% of the compound ("substantially pure"), which is then used or formulated as described herein. Such "substantially pure" compounds of Formula (I), Formula (II), Formula (III), or Formula (IV) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends in Immunology*, 28:102 (2007)).

By virtue of their $S1P_1$ activity as agonists, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, juvenile idiopathic arthritis, systemic lupus erythematosus, cutaneous lupus erythematosus (discoid lupus erythematosus, subacute lupus erythematosus) and lupus nephritis, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, psoriatic arthritis, atopic dermatitis, contact dermatitis, eczematous dermatitis, seborrheic dermatitis, lichen planus, pemphigus, bullous pemphigoid, epidermolysis bullosa, urticaria, angioedemas, vasculitis including ANCA-associated vasculitis, giant cell arteritis, Takayasu's arteritis, microscopic poliangiitis, central nervous system vasculitis, Churg-Strauss Syndrome, and rheumatoid vasculitis, erythema, cutaneous eosinophilia, acne, alopecia areata, keratoconjunctivitis, vernal conjunctivitis, uveitis associated with Behcet's disease, keratitis, herpetic keratitis, conical cornea, dystrophia epithelialis comeae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fasciitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, neuropathic pain, chronic bacterial infection, thrombocytopenia, IgA nephropathy, mesangioproliferative glomerulonephritis, IgG4-related disease, ankylosing spondylitis, and relapsing polychondritis. Juvenile idiopathic arthritis includes oligoarthritis-onset juvenile idiopathic arthritis, polyarthritis-onset juvenile idiopathic arthritis, systemic-onset juvenile idiopathic arthritis, juvenile psoriatic arthritis, and enthesitis-related juvenile idiopathic arthritis.

One embodiment provides a method for treating autoimmune and/or inflammatory diseases, comprising administering to a mammal in need thereof at least one compound of Formula (I), Formula (II), Formula (III), or Formula (IV), or a pharmaceutically acceptable salt thereof. Another embodiment provides the compounds of Formula (I), Formula (II), Formula (III), or Formula (IV), or pharmaceutically acceptable salts thereof, for use in therapy for the treatment of autoimmune and/or inflammatory diseases. In another embodiment, provided is the use of the compounds of Formula (I), Formula (II), Formula (III), or Formula (IV), or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. The method of the present embodiment includes administration of a therapeutically effect amount of a compound of Formula (I), Formula (II), Formula (III), or Formula (IV), or a pharmaceutically effective salt thereof.

In another embodiment, a method for treating vascular disease is provided comprising administering to a mammal in need thereof at least one compound of Formula (I), Formula (II), Formula (III), or Formula (IV), or a pharmaceutically acceptable salt thereof. Another embodiment provides the compounds of Formula (I), Formula (II), Formula (III), or Formula (IV), or pharmaceutically acceptable salts thereof, for use in therapy for the treatment of vascular disease. In another embodiment, provided is the use of the compounds of Formula (I), Formula (II), Formula (III), or Formula (IV), or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

In another embodiment, a method for treating inflammatory bowel disease is provided comprising administering to a mammal in need thereof at least one compound of Formula (I), Formula (II), Formula (III), or Formula (IV) or a pharmaceutically acceptable salt thereof. Another embodiment provides the compounds of Formula (I), Formula (II), Formula (III), or Formula (IV), or pharmaceutically acceptable salts thereof, for use in therapy for the treatment of inflammatory bowel disease. In another embodiment, provided is the use of the compounds of Formula (I), Formula (II), Formula (III), or Formula (IV), or pharmaceutically acceptable salts thereof, for the manufacture of a medicament for treatment of inflammatory bowel disease. A therapeutically effective amount may be employed in these embodiments. Preferably, in these embodiments, the inflammatory bowel disease is selected from Crohn's disease, ulcerative colitis, collagenous colitis, lymphocytic colitis, ischaemic colitis, diversion colitis, Behçet's disease, and indeterminate colitis.

In another embodiment, a method for treating lupus is provided comprising administering to a mammal in need thereof at least one compound of Formula (I), Formula (II), Formula (III), or Formula (IV), or a pharmaceutically acceptable salt thereof. Another embodiment provides the compounds of Formula (I), Formula (II), Formula (III), or Formula (IV), or pharmaceutically acceptable salts thereof, for use in therapy for the treatment of lupus. In another embodiment, provided is the use of the compounds of Formula (I), Formula (II), Formula (III), or Formula (IV), or pharmaceutically acceptable salts thereof, for the manufacture of a medicament for treatment of lupus. A therapeutically effective amount may be employed in these embodiments. Lupus includes systemic lupus erythematosus, cutaneous lupus erythematosus, discoid lupus erythematosus, subacute lupus erythematosus and lupus nephritis.

In another embodiment, a method for treating multiple sclerosis is provided comprising administering to a mammal in need thereof at least one compound of Formula (I), Formula (II), Formula (III), or Formula (IV), or a pharmaceutically acceptable salt thereof. Another embodiment provides the compounds of Formula (I), Formula (II), Formula (III), or Formula (IV), or pharmaceutically acceptable salts thereof, for use in therapy for the treatment of multiple sclerosis. In another embodiment, provided is the use of the compounds of Formula (I), Formula (II), Formula (III), or Formula (IV), or pharmaceutically acceptable salts thereof, for the manufacture of a medicament for treatment of multiple sclerosis. A therapeutically effective amount may be employed in these embodiments. Preferably, in these embodiments, multiple sclerosis includes relapsing remitting multiple sclerosis, primary progressive multiple sclerosis, secondary progressive multiple sclerosis, and progressive relapsing multiple sclerosis.

The methods of treating S1P1-associated conditions may comprise administering compounds of Formula (I), Formula (II), Formula (III), or Formula (IV) alone or in combination with each other and/or other suitable therapeutic agents useful in treating such conditions. Accordingly, "therapeutically effective amount" is also intended to include an amount of the combination of compounds claimed that is effective to act as an agonist at the S1P1 receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo [1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), belatacept, or their ligands including CD154 (GP39, or CD40L); antibodies to, fusion proteins, or soluble receptors of human cytokines or growth factors, for example, TNF such as, infliximab (REMICADE®), etanercept (Embrel), adalimumab (HUMIRA®), LT, Il-1 such as anakinra (KINERET®) (an IL-1 receptor antagonist), IL-2, IL-4, IL-5, Il-6, such as CNTO 328 (a chimeric anti-IL-6 antibody), Il-7, Il-8, Il-12, Il-15, Il-16, Il-17, Il-21, Il-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenolate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I), Formula (II), Formula (III), or Formula (IV) can be administered by any means suitable for the condition to be treated, which can depend on the need for site-specific treatment or quantity of Formula (I), Formula (II), Formula (III), or Formula (IV) compound to be delivered.

Also embraced within this invention is a class of pharmaceutical compositions comprising a compound of Formula (I), Formula (II), Formula (III), or Formula (IV) and one or more non-toxic, pharmaceutically-acceptable carriers and/or diluents and/or adjuvants (collectively referred to herein as "carrier" materials) and, if desired, other active ingredients. The compounds of Formula (I), Formula (II), Formula (III), or Formula (IV) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I), Formula (II), Formula (III), or Formula (IV) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinylpyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I), Formula (II), Formula (III), or Formula (IV) with at least one inert solid diluent, such as, for example, calcium carbonate; calcium phosphate; and kaolin.

Soft gelatin capsules can, for example, be prepared by mixing at least one compound of Formula (I), Formula (II), Formula (III), or Formula (IV) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I), Formula (II), Formula (III), or Formula (IV) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinylpyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I), Formula (II), Formula (III), or Formula (IV) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I), Formula (II), Formula (III), or Formula (IV) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I), Formula (II), Formula (III), or Formula (IV) thereof can, for example, be prepared as an oil-in-water emulsion. The oily phase of the emulsions comprising compounds of Formula (I), Formula (II), Formula (III), or Formula (IV) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I), Formula (II), Formula (III), and Formula (IV) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I), Formula (II), Formula (III), and Formula (IV) in an oily phase, such as, for example, a mixture of soybean oil and lecithin; 2) combining the Formula (I), Formula (II), Formula (III), and/or Formula (IV) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I), Formula (II), Formula (III), and Formula (IV) and optionally an additional agent selected from any pharmaceutically acceptable carrier, adjuvant, and vehicle. Alternate compositions of this invention comprise a compound of the Formula (I), Formula (II), Formula (III), or Formula (IV) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, Greene's Protective Groups in Organic Synthesis, Fourth Edition, Wiley and Sons (2007).

Scheme 1 illustrates a method suitable for the preparation of compounds of Formula (I). The corresponding tetralone 1 can be synthesized based on literature (WO 2006/028959 A1). This ketone can undergo oxidative condensation with reagents such as thioureas to afford the corresponding aminothiazole 2 (Bioorg. Med. Chem. Let. 2002, 12, 1563-1566). The Sandmeyer reaction can than install the desired halide 3 (Bioorg. Med. Chem. Let. 2010, 20, 5879-5882; Synthesis 2012, 44, 1026-1029; J. Med. Chem. 2016, 59, 2760-2779). Alternatively, aminothiazole 2 can undergo reductive amination reaction leading to alkylated aminothiazole 4 (Comprehensive Organic Synthesis; Trost, B. N., Fleming, I., Eds.; Pergamon Press: New York, 1991; Vol. 8).

Scheme 2 shows different diversification of halide 3. It can react with Grignard reagents under Fe(III) catalysis leading to amino alcohol 5 after hydrolysis (*J. Am. Chem. Soc.,* 2002, 124, 13856-13863). The halide can also be displaced by alcohols (J. Med. Chem. 2009, 52, 3689-3702) or thiols (Angew. Chem. Int. Ed. 1998, 37, 84-87) in the presence of a hindered base affording amino alcohol 6 after hydrolysis. Alternatively, halide 3 can undergo Suzuki coupling (J. Organometallic Chem. 1999, 576, 147-168) or Buchwald-Hartwig coupling (Acc. Chem. Res. 1998, 31, 852; Acc. Chem. Res. 1998, 31, 805) leading to aminoalcohols 7 and 8, respectively after hydrolysis.

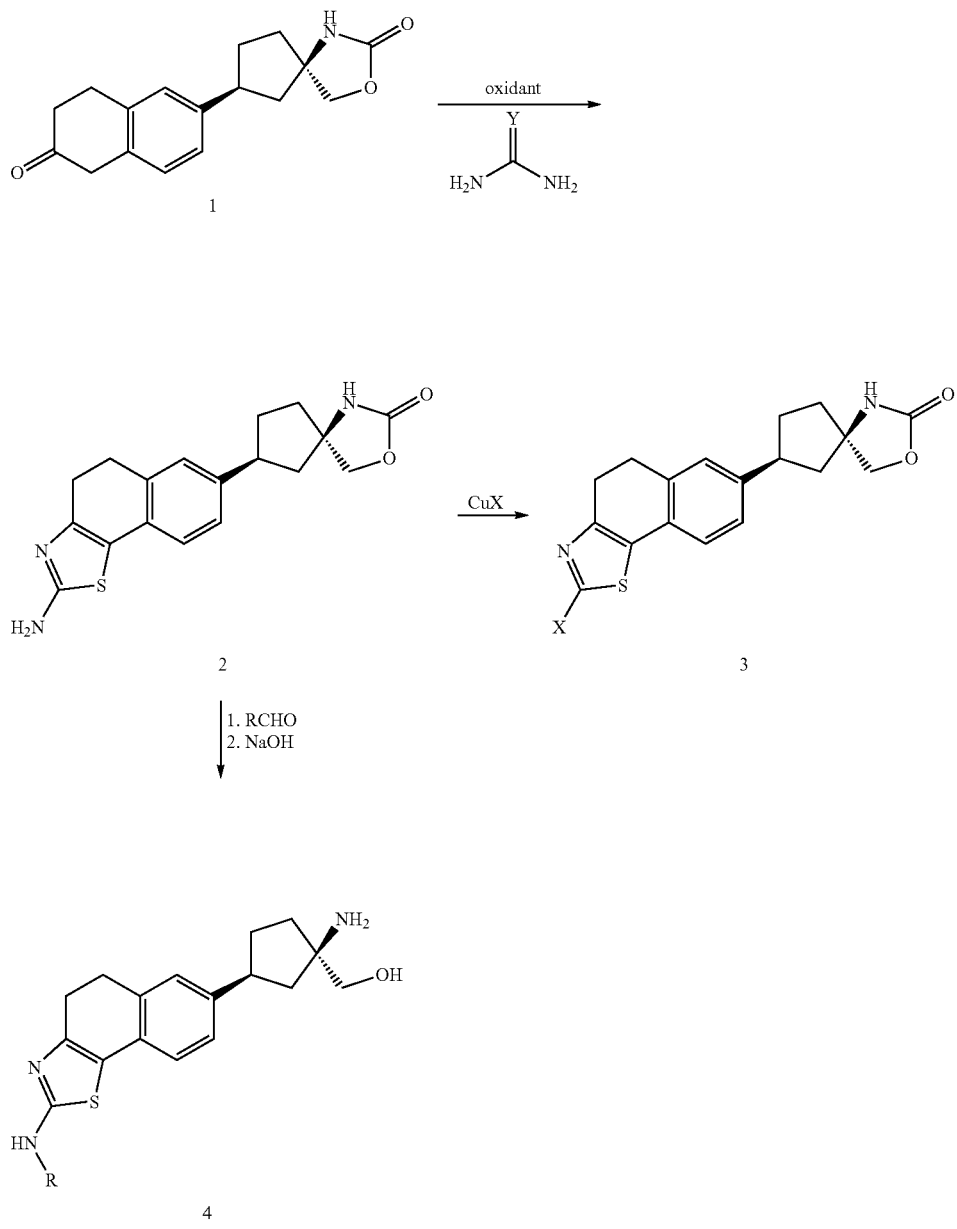

SCHEME 1

SCHEME 2

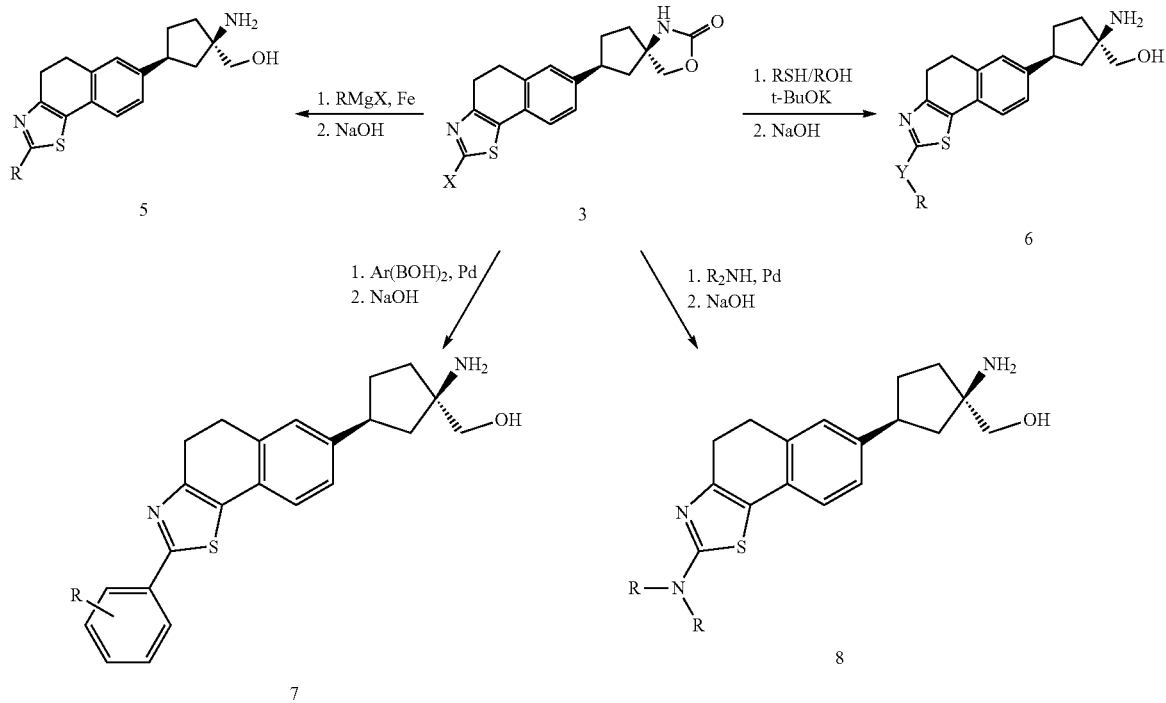

Scheme 3 shows the conversion of amino alcohols 5 to the corresponding active metabolite phosphates using pyrophosphoryl chloride.

SCHEME 3

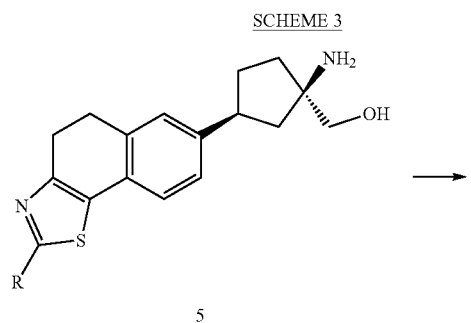

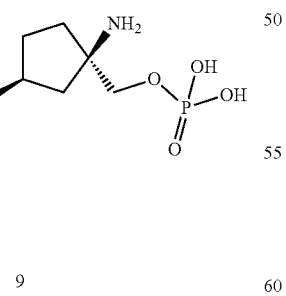

SCHEME 4

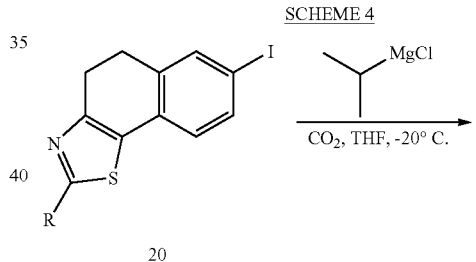

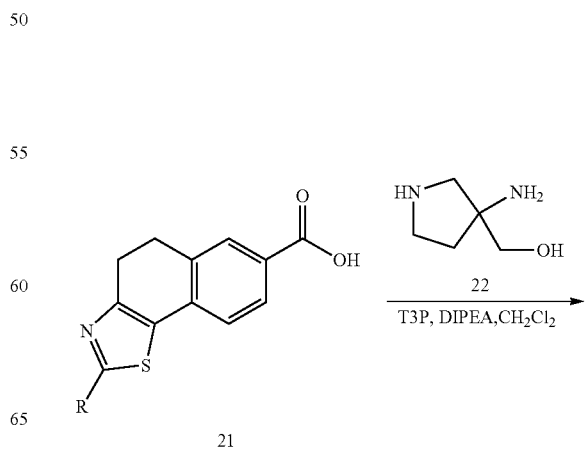

Schemes 4 and 5 illustrate methods for the preparation of tricyclic carboxamide compounds of Formula (IV) through the preparation of substituted 4,5-dihydronaphtho[2,1-d]thiazole-7-carboxylic acids from either iodo or vinyl precursors.

25
-continued

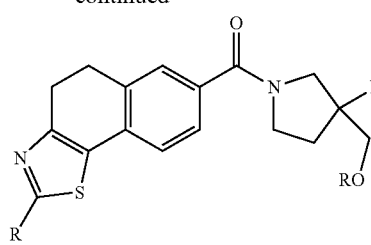
23

P₂O₃Cl₄ CH₃CN  R = H
R = PO(OH)₂
24

SCHEME 5

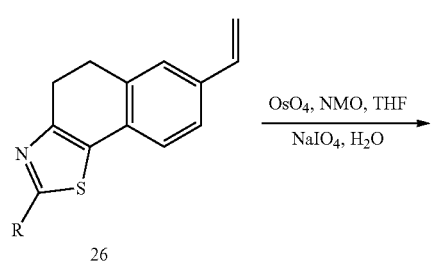
26

OsO₄, NMO, THF
NaIO₄, H₂O

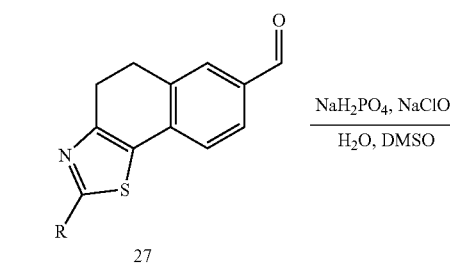
27

NaH₂PO₄, NaClO₂
H₂O, DMSO

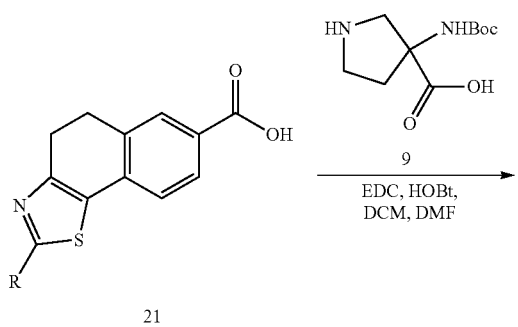
21

EDC, HOBt,
DCM, DMF

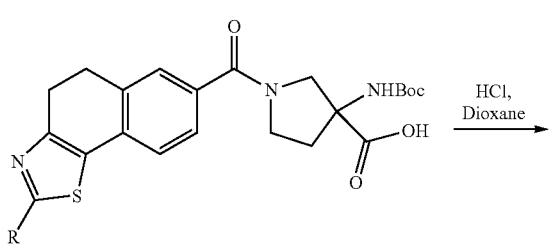
28

HCl,
Dioxane

26
-continued

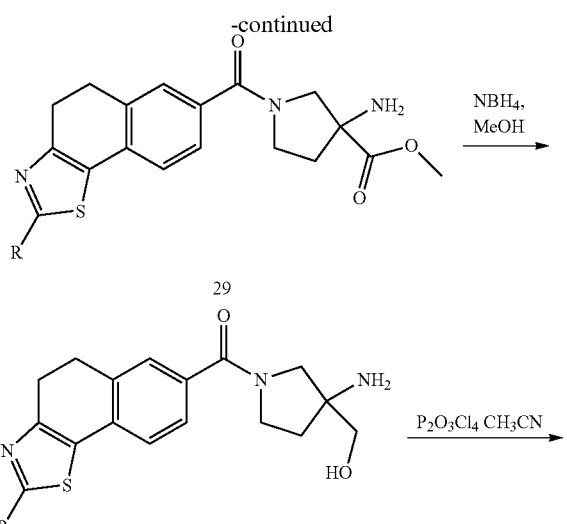

NBH₄, MeOH

29

P₂O₃Cl₄ CH₃CN

23

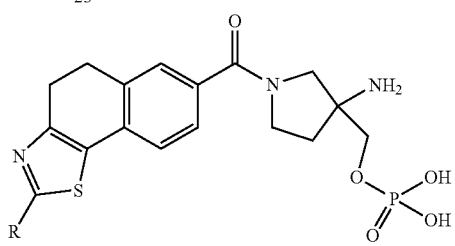
24

EXAMPLES

Common intermediates are generally useful for the preparation of more than one Example and are identified sequentially (e.g., Intermediate 1, Intermediate 2, etc.) and are abbreviated as Int. 1 or I1, Int. 2 or I2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

Column chromatography was generally performed using the flash chromatography technique (*J. Org. Chem.* 1978, 43, 2923), or with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters SunFire C18, Waters XBridge C18, PHENOMENEX Axia C18, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chiral super-critical fluid chromatographic separation of enantiomers or pairs of diastereomers was performed using conditions described for the individual cases. Mass spectral data were obtained by liquid chromatography mass spectroscopy using electrospray ionization.

HPLC Conditions

Condition A: (Analytical)
Waters Acquity UPLC BEH C18 (2.1×50) mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Condition B: (Preparative)
Shimatzu prep HPLC, Luna® C18 30×100 mm, 5 μm (Phenomenex Inc.); 2 mL injection; Mobile Phase A=0.1% TFA in Water; Mobile Phase B=0.1% TFA in MeCN; Temperature: 25° C.; Gradient: 20-100% B over 5 min, then a 10 min hold at 100% B, Flow: 30 mL/min; Detection: UV at 220 nm.

Condition G: Column: Waters Acquity BEH C18 2.1×50 mm 1.7 μm; Linear gradient of 0-100% solvent B over 3 min, then 0.75 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Temperature=50° C.; Products detected at 220 nm wavelength.

Condition K: Column: BEH C18 2.1×50 mm 1.7 um, Linear gradient of 0-100% solvent B over 1.5 min, then 0.7 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Temperature=50° C.; Products detected at 220 nm wavelength.

ABBREVIATIONS

Ac acetyl
ACN acetonitrile
AcOH acetic acid
anhyd. anhydrous
aq. aqueous
BH$_3$DMS boron dimethylsulfide
Bn benzyl
Bu butyl
Boc tert-butoxycarbonyl
BOP benzotriazol-1-yloxytris-(dimethylamino)-phosphonium hexafluorophosphate
CV Column Volumes
DAST (diethylamino)sulfur trifluoride
DCE dichloroethane
DCM dichloromethane
DMAP dimethylaminopyridine
DEA diethylamine
DIPEA diisopropylethylamine
DMF dimethylformamide
DMSO dimethylsulfoxide
EDC 1-(3-dimethylaminopropyl)-3-ethylcarbodiimide hydrochloride
EtOAc ethyl acetate
Et ethyl
EtOH ethanol
H or H$_2$ hydrogen
h, hr or hrs hour(s)
HATU O-(7-azabenzotriazol-1-yl)-N,N,N',N'-tetramethyluronium hexafluorophosphate
HCl hydrochloric acid
HCTU O-(6-Chlorobenzotriazol-1-yl)-N,N,N',N'-tetramethyluronium hexafluorophosphate
hex hexane
HOAc acetic acid
HOBt hydroxybenzotriazole
HPLC high pressure liquid chromatography
i iso
IPA isopropyl alcohol
LC liquid chromatography
M molar
mM millimolar
Me methyl
MeOH methanol
MHz megahertz
min. minute(s)
mins minute(s)
M$^{+1}$ (M+H)$^+$
MS mass spectrometry
n or N normal
NBS n-bromosuccinimide
nm nanometer
nM nanomolar
NCS N-chlorosuccinimide
NMO N-methylmorpholine-N-oxide
NMP N-methylpyrrolidine
Pd/C palladium on carbon
PdCl$_2$(dppf)$_2$ [1,1'-bis(diphenylphosphino)ferrocene]dichloropalladium(II)
Pd(PPh$_3$)$_4$ tetrakis(triphenylphosphine)palladium
Ph phenyl
PPh$_3$ triphenylphosphine
Pr propyl
PSI pounds per square inch
PyBOP bromotripyrrolidinophosphonium hexafluorophosphate
Ret Time retention time
sat. saturated
SFC supercritical fluid chromatography
TEA triethylamine
TFA trifluoroacetic acid
THF tetrahydrofuran

Intermediate I-1

(5R,7S)-7-(2-halo-4,5-dihydronaphtho[2,1-d]thiazol-7-yl)-3-oxa-1-azaspiro[4.4]nonan-2-one

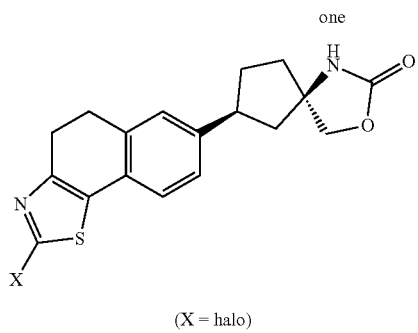

(I-1)

(X = halo)

Intermediate I-1A: (5R,7S)-7-(2-amino-4,5-dihydronaphtho[2,1-d]thiazol-7-yl)-3-oxa-1-azaspiro[4.4]nonan-2-one, Hydroiodinic Acid Salt (I-1A)

(5R,7S)-7-(6-oxo-5,6,7,8-tetrahydronaphthalen-2-yl)-3-oxa-1-azaspiro[4.4]nonan-2-one (200 mg, 0.7 mmol) (WO 2006/028959 A1) was dissolved in ethanol (1.4 mL) in a screw cap vial. Thiourea (187 mg, 2.5 mmol) and iodine (196 mg, 0.77 mmol) were then added at room temperature. The tube was sealed and heated to 100° C. for 2 h. LCMS analysis revealed full conversion of starting material. The tube was unsealed allowing the reaction mixture to concentrate for 15 min at 100° C. Upon cooling to room temperature, the desired product precipitated out. Addition of 1 mL of water, stirring an additional 15 min followed by filtration afforded the desired compound (5R,7S)-7-(2-amino-4,5-dihydronaphtho[2,1-d]thiazol-7-yl)-3-oxa-1-azaspiro[4.4]nonan-2-one, hydroiodinic acid salt (200 mg, 61%) as a brown solid. LCMS (M+H): 342.3; LC retention time: 0.64 min (analytical HPLC Method A), $^1$H NMR (400 MHz, METHANOL-$d_4$) δ 7.23 (s, 1H), 7.21-7.15 (m, 1H), 7.06 (d, J=7.9 Hz, 1H), 4.40 (d, J=8.6 Hz, 1H), 4.31 (d, J=8.6 Hz, 1H), 3.17-3.03 (m, 3H), 2.93-2.81 (m, 2H), 2.34 (dd, J=13.0, 7.3 Hz, 1H), 2.22-2.08 (m, 2H), 2.04-1.76 (m, 3H).

Intermediate I-1B: (5R,7S)-7-(2-iodo-4,5-dihydronaphtho[2,1-d]thiazol-7-yl)-3-oxa-1-azaspiro[4.4]nonan-2-one

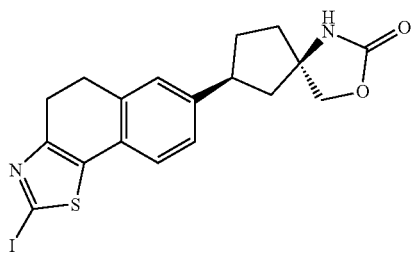

(I-1B)

To a suspension of (5R,7S)-7-(2-amino-4,5-dihydronaphtho[2,1-d]thiazol-7-yl)-3-oxa-1-azaspiro[4.4]nonan-2-one, hydroiodinic salt (50 mg, 0.1 mmol) and copper(I) iodide (31 mg, 0.16 mmol) in acetonitrile (2.2 mL) was added tert-butyl nitrite (20 μL, 0.15 mmol) at 0° C. The reaction mixture was stirred at this temperature for 15 min and at room temperature overnight when LCMS analysis showed complete consumption of starting material. The mixture was diluted with EtOAc and filtered through Celite. The resulting solution was concentrated under reduced pressure. LCMS (M+H): 453.1; LC retention time: 1.01 min (analytical HPLC Method A).

Intermediate I-1C: (5R,7S)-7-(2-chloro-4,5-dihydronaphtho[2,1-d]thiazol-7-yl)-3-oxa-1-azaspiro[4.4]nonan-2-one

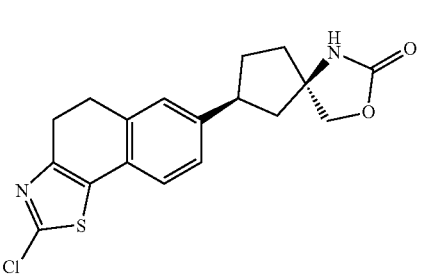

(I-1C)

A solution (5R,7S)-7-(2-amino-4,5-dihydronaphtho[2,1-d]thiazol-7-yl)-3-oxa-1-azaspiro[4.4]nonan-2-one, iodinic acid (38 mg, 0.08 mmol) in EtOAc (25 mL) was washed once with 1 N NaOH (25 mL). The organic layer was dried over sodium sulfate and filtered. To the organic solution was added TFA (100 μL) and the solution was concentrated under reduced pressure. The residue was dissolved in acetonitrile (1.7 mL). To this solution was added copper(I) chloride (12 mg, 0.13 mmol) followed by tert-butyl nitrite (15 μL, 0.12 mmol) at 0° C. The reaction mixture was stirred at this temperature for 15 min and at room temperature overnight. LCMS analysis showed complete consumption of starting material. The mixture was diluted with 2 mL of MeOH and purified by HPLC using condition B affording (5R,7S)-7-(2-chloro-4,5-dihydronaphtho[2,1-d]thiazol-7-yl)-3-oxa-1-azaspiro[4.4]nonan-2-one (12 mg, 0.033 mmol, 40% yield) as a brown solid.

Example 1

((1R,3S)-1-amino-3-(2-heptyl-4,5-dihydronaphtho[2,1-d]thiazol-7-yl)cyclopentyl) methanol, TFA Salt

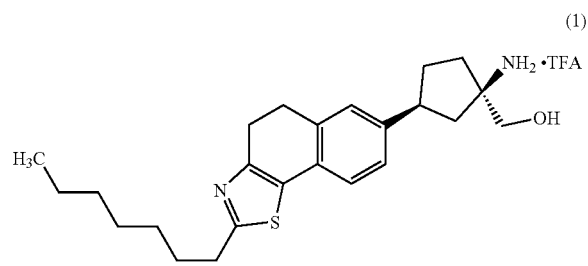 [SMILES: CCCCCCCc1nc2c(s1)-c1ccc([C@H]3CC[C@](N)(CO)C3)cc1CC2]

(1)

To a solution of (5R,7S)-7-(2-chloro-4,5-dihydronaphtho[2,1-d]thiazol-7-yl)-3-oxa-1-azaspiro[4.4]nonan-2-one (14 mg, 0.04 mmol) and iron(III) acac (1.40 mg, 3.9 μmol) in a mixture of THF (0.5 mL) and N-methyl-2-pyrrolidinone (0.1 mL) was added a 1 M heptylmagnesium bromide (0.12 mL, 0.12 mmol) at room temperature. Analysis of the reaction by LCMS after 15 min showed full conversion. The reaction mixture was diluted with diethyl ether and was quenched by the addition of 1N HCl. The aqueous layer was back extracted twice with EtOAc. The organic layer were combined, dried with $MgSO_4$ and concentrated under reduced pressure. The resulting oil was dissolved in dioxane (1 mL) followed by the addition of NaOH (0.56 mL, 0.56 mmol). The solution was warmed to 100° C. and stirred for 3 h. LCMS showed complete conversion. The solution was injected on HPLC using Condition B providing ((1R,3S)-1-amino-3-(2-heptyl-4,5-dihydronaphtho[2,1-d]thiazol-7-yl)cyclopentyl)methanol, TFA (3 mg, 5.6 μmol, 15% yield, 2 steps) as a yellow solid. LCMS (M+H): 399.5; LC retention time: 0.94 min (analytical HPLC Method A); $^1$H NMR (400 MHz, METHANOL-$d_4$) δ 7.26-7.13 (m, 3H), 3.65 (dd, J=14.7, 12.1 Hz, 2H), 3.26-3.12 (m, 1H), 3.12-2.91 (m, 4H), 2.47 (dd, J=13.4, 7.0 Hz, 1H), 2.25-2.11 (m, 1H), 2.08-1.91 (m, 3H), 1.90-1.70 (m, 2H), 1.53-1.25 (m, 10H), 0.93 (t, J=6.8 Hz, 3H).

The examples in Table 1 were prepared according to the general procedure described in Example 1, by employing the appropriate Grignard reagents.

TABLE 1

| Ex. No. | Structure | MS observed ($M^{+1}$) | HPLC ret. time (min.) | HPLC method |
|---|---|---|---|---|
| 2 | 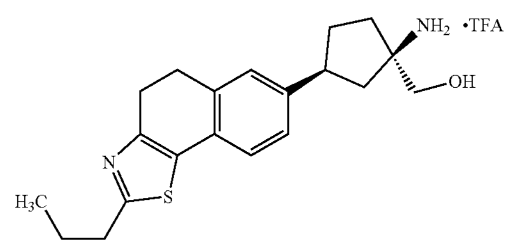 [SMILES: CCCc1nc2c(s1)-c1ccc([C@H]3CC[C@](N)(CO)C3)cc1CC2] | 343.2 | 0.76 | A |
| 3 | 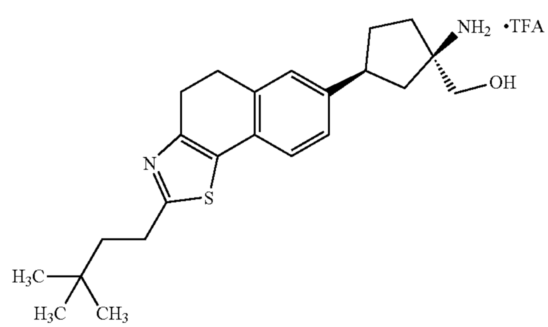 [SMILES: CC(C)(C)CCc1nc2c(s1)-c1ccc([C@H]3CC[C@](N)(CO)C3)cc1CC2] | 460.3 | 0.86 | A |
| 4 | 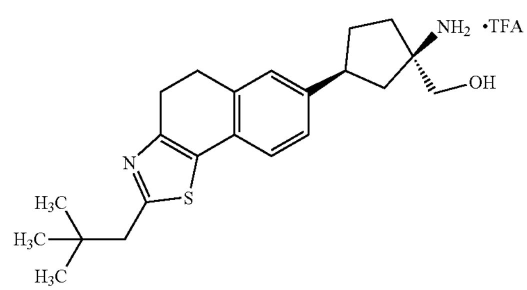 [SMILES: CC(C)(C)Cc1nc2c(s1)-c1ccc([C@H]3CC[C@](N)(CO)C3)cc1CC2] | 371.2 | 0.80 | A |

TABLE 1-continued

| Ex. No. | Structure | MS observed (M+1) | HPLC ret. time (min.) | HPLC method |
|---|---|---|---|---|
| 5 | 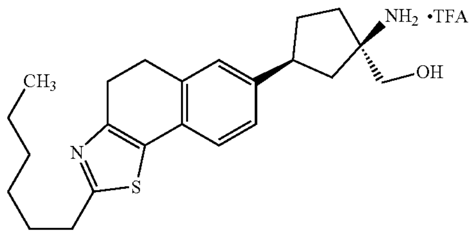 [SMILES: CCCCCCc1nc2c(s1)-c1ccc([C@H]3CC[C@](N)(CO)C3)cc1CC2] | 385.6 | 0.89 | A |
| 6 | 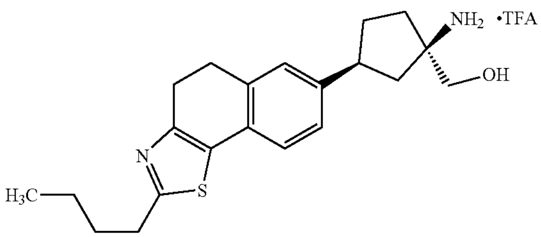 [SMILES: CCCCc1nc2c(s1)-c1ccc([C@H]3CC[C@](N)(CO)C3)cc1CC2] | 357.3 | 0.80 | A |

Example 7

((1R,3S)-1-amino-3-(2-(2-butoxyethoxy)-4,5-dihydronaphtho[2,1-d]thiazol-7-yl) cyclopentyl)methanol, Trifluoroacetic Acid Salt

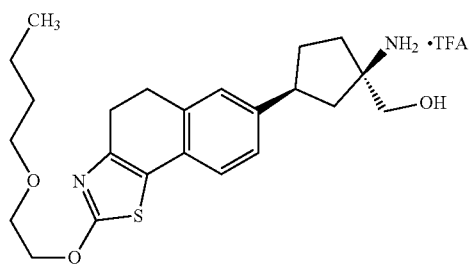

(7)

To a solution of (5R,7S)-7-(2-chloro-4,5-dihydronaphtho[2,1-d]thiazol-7-yl)-3-oxa-1-azaspiro[4.4]nonan-2-one (3 mg, 8 μmol) in dioxane (0.5 mL) was added 2-butoxyethanol (20 mg, 0.17 mmol) followed by potassium tert-butoxide (9 mg, 0.08 mmol) at room temperature. The mixture was stirred at 70° C. for 2 h when LCMS showed complete consumption of starting material. To this mixture was added a 1 M NaOH solution (0.5 mL, 0.500 mmol) at room temperature. The mixture was heated to 70° C. and stirred for 14 h. LCMS showed complete consumption of the intermediate. The solution was injected on the HPLC prep using condition B affording ((1R,3S)-1-amino-3-(2-(2-butoxyethoxy)-4,5-dihydronaphtho[2,1-d]thiazol-7-yl)cyclopentyl) methanol, TFA (3 mg, 5.5 μmol, 66% yield) as a white solid. LCMS (M+H): 417.3; LC retention time: 0.87 min (analytical HPLC Method A), $^1$H NMR (400 MHz, METHANOL-$d_4$) δ 7.17 (s, 1H), 7.13 (dd, J=7.8, 1.4 Hz, 1H), 7.03 (d, J=7.9 Hz, 1H), 4.60-4.49 (m, 2H), 3.87-3.77 (m, 2H), 3.65 (dd, J=13.2, 10.8 Hz, 2H), 3.56 (t, J=6.5 Hz, 2H), 3.24-3.10 (m, 1H), 3.03 (t, J=7.0 Hz, 2H), 2.83 (t, J=8.4 Hz, 2H), 2.51-2.41 (m, 1H), 2.24-2.09 (m, 1H), 2.05-1.89 (m, 3H), 1.75 (t, J=12.7 Hz, 1H), 1.68-1.52 (m, 2H), 1.49-1.33 (m, 2H), 0.95 (t, J=7.4 Hz, 3H).

The examples in Table 2 were prepared according to the general procedure described in Example 7, by employing the appropriate alcohol or thiol.

TABLE 2

| Ex. No. | Structure | MS observed (M+1) | HPLC ret. time (min.) | HPLC method |
|---|---|---|---|---|
| 8 | 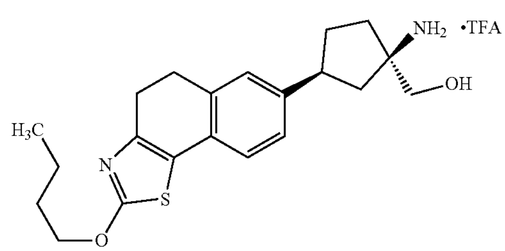 [SMILES: CCCCOc1nc2c(s1)-c1ccc([C@H]3CC[C@](N)(CO)C3)cc1CC2] | 373.3 | 0.84 | A |

TABLE 2-continued

| Ex. No. | Structure | MS observed ($M^{+1}$) | HPLC ret. time (min.) | HPLC method |
|---|---|---|---|---|
| 9 | H₃C—(chain)—[4,5-dihydronaphtho[2,1-d]thiazole with OCH₂ linker]—cyclopentyl(NH₂·TFA)(CH₂OH) | 401.3 | 0.98 | A |
| 10 | H₃C—(chain)—[4,5-dihydronaphtho[2,1-d]thiazole with SCH₂ linker]—cyclopentyl(NH₂·TFA)(CH₂OH) | 389.3 | 0.89 | A |
| 11 | CH₃—(chain)—[4,5-dihydronaphtho[2,1-d]thiazole with S linker]—cyclopentyl(NH₂·TFA)(CH₂OH) | 403.2 | 0.93 | A |
| 12 | CH₃—(chain)—[4,5-dihydronaphtho[2,1-d]thiazole with O linker]—cyclopentyl(NH₂·TFA)(CH₂OH) | 387.2 | 0.90 | A |

Example 13

((1R,3S)-1-amino-3-(2-(hexyloxy)naphtho[2,1-d]thiazol-7-yl)cyclopentyl)methanol, Trifluoroacetic Acid Salt

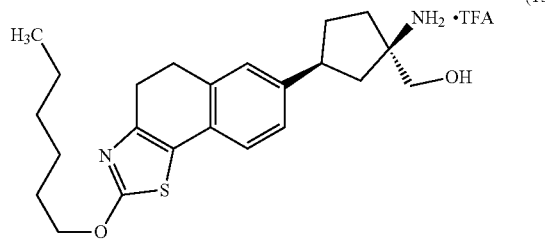

(13)

To a solution of ((1R,3S)-1-amino-3-(2-(hexyloxy)-4,5-dihydronaphtho[2,1-d]thiazol-7-yl)cyclopentyl)methanol, TFA (8 mg, 0.016 mmol) in MeCN (1.6 mL) was added copper(II) chloride (21 mg, 0.16 mmol). The reaction mixture was stirred at room temperature overnight open to air. LCMS showed full conversion. The reaction mixture was diluted with MeOH and injected on HPLC prep using Condition B affording ((1R,3S)-1-amino-3-(2-(hexyloxy)naphtho[2,1-d]thiazol-7-yl)cyclopentyl)methanol, TFA (5 mg, 9.3 µmol, 60% yield). LCMS (M+H): 399.2; LC retention time: 1.00 min (analytical HPLC Method A); $^1$H NMR (400 MHz, METHANOL-$d_4$) δ 7.90-7.79 (m, 3H), 7.76 (d, J=8.6 Hz, 1H), 7.58 (dd, J=8.6, 1.8 Hz, 1H), 4.61 (t, J=6.6 Hz, 2H), 3.70 (dd, J=16.3, 11.9 Hz, 2H), 3.47-3.37 (m, 1H), 2.58 (dd, J=13.2, 6.2 Hz, 1H), 2.35-2.24 (m, 1H), 2.17-1.97 (m, 3H), 1.97-1.81 (m, 3H), 1.62-1.49 (m, 2H), 1.49-1.35 (m, 4H), 0.96 (t, J=7.0 Hz, 3H).

The examples in Table 3 were prepared according to the general procedure described in Example 13, by employing the appropriate tricyclic intermediate.

TABLE 3

| Ex. No. | Structure | MS observed (M+1) | HPLC ret. time (min.) | HPLC method |
|---|---|---|---|---|
| 14 | (structure) | 387.2 | 0.90 | A |
| 15 | (structure) | 385.2 | 0.92 | A |
| 16 | (structure) | 371.2 | 0.87 | A |

Example 17

((1R,3S)-1-amino-3-(2-(butylamino)-4,5-dihydronaphtho[2,1-d]thiazol-7-yl)cyclopentyl)methanol, Trifluoroacetic Acid Salt

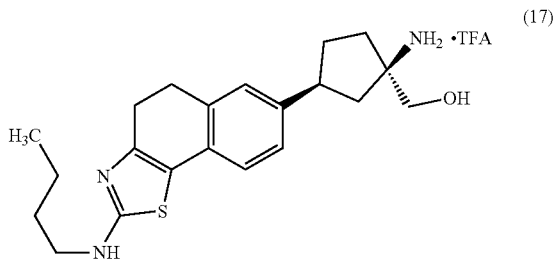 [SMILES: CCCCNc1nc2c(s1)-c1ccc([C@H]3CC[C@](N)(CO)C3)cc1CC2]

(17)

To a solution of (5R,7S)-7-(2-amino-4,5-dihydronaphtho[2,1-d]thiazol-7-yl)-3-oxa-1-azaspiro[4.4]nonan-2-one (50 mg, 0.15 mmol) in MeOH (15 mL) was added butyraldehyde (53 mg, 0.73 mmol). The reaction mixture was heated to 70° C. for 1 h and then cooled down to room temperature. Sodium borohydride (55 mg, 1.5 mmol) was then added and the solution was stirred 30 min. LCMS showed complete consumption. LCMS (M+H): 398.4; LC retention time: 0.75 min (analytical HPLC Method A). The solvent was removed under reduced pressure and diluted in EtOAc. The organic layer was washed with 1 N NaOH, dried over sodium sulfate, filtered and concentrated under reduced pressure. The resulting oil was dissolved in dioxane (0.7 mL) followed by the addition of sodium hydroxide (1M, 150 µL, 0.15 mmol). The solution was warmed to 100° C. and stirred for 2 h. LCMS showed complete conversion. The solution was injected on HPLC using Condition B providing ((1R,3S)-1-amino-3-(2-(butylamino)-4,5-dihydronaphtho[2,1-d]thiazol-7-yl)cyclopentyl)methanol, 2 TFA (12 mg, 0.019 mmol) as a white solid. LCMS (M+H): 372.3; LC retention time: 0.61 min (analytical HPLC Method A); $^1$H NMR (400 MHz, METHANOL-$d_4$) δ 7.23 (s, 1H), 7.22-7.16 (m, 1H), 7.08 (d, J=7.7 Hz, 1H), 3.71-3.58 (m, 2H), 3.47 (t, J=7.2 Hz, 2H), 3.23-3.14 (m, 1H), 3.11 (t, J=8.1 Hz, 2H), 2.89 (t, J=8.1 Hz, 2H), 2.52-2.42 (m, 1H), 2.23-2.09 (m, 1H), 2.05-1.91 (m, 3H), 1.83-1.68 (m, 3H), 1.50 (dq, J=15.0, 7.5 Hz, 2H), 1.03 (t, J=7.4 Hz, 3H).

Example 18

((1R,3S)-1-amino-3-(2-(butyl(methyl)amino)-4,5-dihydronaphtho[2,1-d]thiazol-7-yl) cyclopentyl)methanol, Trifluoroacetic Acid Salt

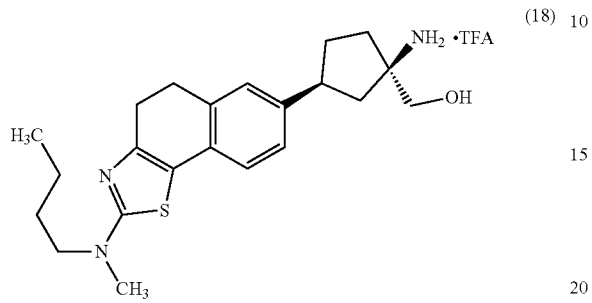

(18)

Example 19

((1R,3S)-1-amino-3-(2-(p-tolyl)-4,5-dihydronaphtho[2,1-d]thiazol-7-yl)cyclopentyl)methanol, Trifluoroacetic Acid Salt

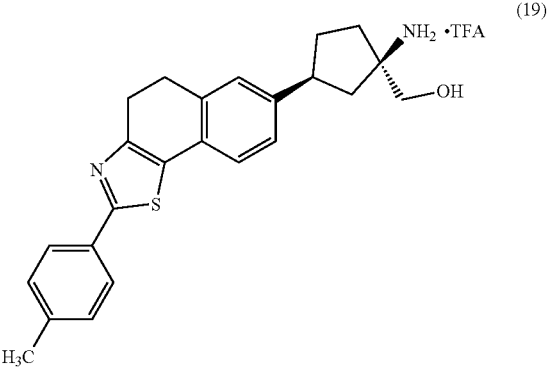 [SMILES: Cc1ccc(-c2nc3c(s2)-c2ccc([C@H]4CC[C@](N)(CO)C4)cc2CC3)cc1]

(19)

To a suspension of (5R,7S)-7-(2-chloro-4,5-dihydronaphtho[2,1-d]thiazol-7-yl)-3-oxa-1-azaspiro[4.4]nonan-2-one (20 mg, 0.055 mmol) in toluene (500 μL) was added N-methylbutan-1-amine (13 μL, 0.11 mmol) followed by potassium tert-butoxide (19 mg, 0.17 mmol), dicyclohexyl(2',4',6'-triisopropyl-[1,1'-biphenyl]-2-yl)phosphine (5 mg, 0.011 mmol), and $Pd_2(dba)_3$ (3 mg, 0.003 mmol) at room temperature. The mixture was then heated to 70° C. and stirred for 1 h. LCMS showed complete consumption of starting material. The mixture was partitioned between water and EtOAc. The aqueous solution was back extract twice with EtOAc. The organic layers were combined, dried and concentrated under reduced pressure. LCMS (M+H): 412.3; LC retention time: 0.79 min (analytical HPLC Method A). The resulting oil was dissolved in dioxane (0.5 mL) and NaOH (705 μl, 0.705 mmol) was added. The mixture was heated at 100° C. for 3 h. LCMS showed complete consumption of starting material. The solution was worked up using EtOAc and water. The organic layer was dried over sodium sulfate and concentrated under reduced pressure. The resulting oil was solubilized in MeOH and injected on the HPLC prep using Condition B afforded ((1R,3S)-1-amino-3-(2-(butyl(methyl)amino)-4,5-dihydronaphtho[2,1-d]thiazol-7-yl)cyclopentyl)methanol, 2 TFA (5 mg, 7.9 μmol, 11% yield) as a white solid. LCMS (M+H): 386.2; LC retention time: 0.63 min (analytical HPLC Method A). $^1H$ NMR (400 MHz, METHANOL-$d_4$) δ 7.20 (s, 1H), 7.18 (d, J=7.7 Hz, 1H), 7.07 (d, J=7.7 Hz, 1H), 3.73-3.57 (m, 4H), 3.28 (s, 3H), 3.23-3.14 (m, 1H), 3.08 (t, J=8.0 Hz, 2H), 2.88 (t, J=8.0 Hz, 2H), 2.52-2.41 (m, 1H), 2.17 (br. s., 1H), 2.05-1.90 (m, 3H), 1.84-1.69 (m, 3H), 1.45 (dd, J=15.2, 7.5 Hz, 2H), 1.03 (t, J=7.4 Hz, 3H)

To a solution of (5R,7S)-7-(2-chloro-4,5-dihydronaphtho[2,1-d]thiazol-7-yl)-3-oxa-1-azaspiro[4.4]nonan-2-one (20 mg, 0.055 mmol) in dioxane (550 μL) was added p-tolylboronic acid (38 mg, 0.28 mmol) and sodium carbonate (55 μL, 0.11 mmol). The reaction mixture was purged with nitrogen followed by the addition of dichloro[1,1'-bis(diphenylphosphino)ferrocene]palladium (II) (2 mg, 2.78 μmol). The reaction mixture was heated to 100° C. and LCMS showed complete conversion after 1 h. LCMS (M+H): 417.1; LC retention time: 1.12 min (analytical HPLC Method A). The solution was cooled to room temperature and NaOH (1M, 554 μL, 0.554 mmol) was then added. The reaction mixture was heated to 100° C. and LCMS showed complete conversion after 6 h. The solution was diluted with EtOAc and water. The aqueous layer was back extracted with EtOAc twice. The organic fraction were combined, dried over sodium sulfate, filtered and concentrated under reduced pressure. The resulting solid was solubilized in MeOH and purified on HPLC prep using Condition B affording ((1R,3S)-1-amino-3-(2-(p-tolyl)-4,5-dihydronaphtho[2,1-d]thiazol-7-yl)cyclopentyl)methanol, TFA (8 mg, 0.015 mmol, 27% yield). LCMS (M+H): 391.2; LC retention time: 0.87 min (analytical HPLC Method A), $^1H$ NMR (400 MHz, METHANOL-$d_4$) δ 7.86 (d, J=8.1 Hz, 2H), 7.32 (dd, J=7.8, 5.4 Hz, 3H), 7.28-7.17 (m, 2H), 3.66 (dd, J=15.4, 11.4 Hz, 2H), 3.14-3.01 (m, 4H), 2.49 (dd, J=13.3, 7.2 Hz, 1H), 2.43 (s, 3H), 2.20 (br. s., 1H), 2.08-1.92 (m, 3H), 1.77 (t, J=12.8 Hz, 1H).

The example in Table 4 were prepared according to the general procedure described in Example 19, by employing the appropriate boronic acid.

TABLE 4

| Ex. No. | Structure | MS observed ($M^{+1}$) | HPLC ret. time (min.) | HPLC method |
|---|---|---|---|---|
| 20 | 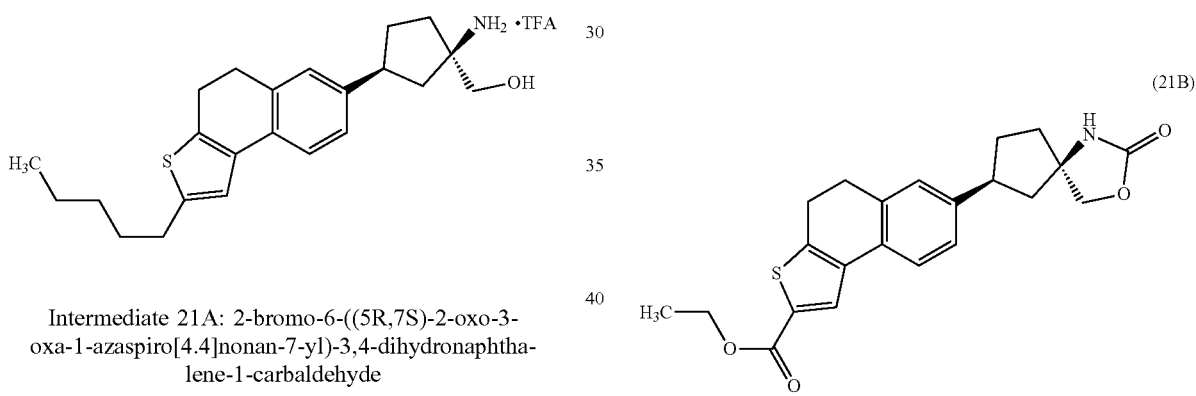 | 407.3 | 0.82 | A |

Example 21

((1R,3S)-1-amino-3-(2-pentyl-4,5-dihydronaphtho[2,1-b]thiophen-7-yl) cyclopentyl)methanol, Trifluoroacetic Acid Salt (21)

Intermediate 21A: 2-bromo-6-((5R,7S)-2-oxo-3-oxa-1-azaspiro[4.4]nonan-7-yl)-3,4-dihydronaphthalene-1-carbaldehyde (21A)

To a solution of DMF (611 μL, 7.9 mmol) in DCM (2.5 mL) was added PBr$_3$ (8.8 mL, 8.8 mmol). The solution was stirred for 1 h at room temperature. To this solution was added (5R,7S)-7-(6-oxo-5,6,7,8-tetrahydronaphthalen-2-yl)-3-oxa-1-azaspiro[4.4]nonan-2-one (250 mg, 0.88 mmol) in DCM (2.5 mL). The reaction mixture was stirred at room temperature for 1 h when LCMS showed complete consumption of the starting material. The reaction mixture was diluted with DCM, washed twice with NaHCO$_3$, dried over sodium sulfate, and concentrated to afford 2-bromo-6-((5R,7S)-2-oxo-3-oxa-1-azaspiro[4.4]nonan-7-yl)-3,4-dihydronaphthalene-1-carbaldehyde (332 mg, 101%). LCMS (M+H): 378.0; LC retention time: 0.93 min (analytical HPLC Method A).

Intermediate 21B: ethyl 7-((5R,7S)-2-oxo-3-oxa-1-azaspiro[4.4]nonan-7-yl)-4,5-dihydronaphtho[2,1-b]thiophene-2-carboxylate (21B)

To a solution of 2-bromo-6-((5R,7S)-2-oxo-3-oxa-1-azaspiro[4.4]nonan-7-yl)-3,4-dihydronaphthalene-1-carbaldehyde (330 mg, 0.88 mmol) and ethyl 2-mercaptoacetate (97 μL, 0.88 mmol) in EtOH (5.8 mL) was added sodium ethoxide (298 mg, 4.4 mmol) in one portion at room temperature. The reaction mixture was stirred at this temperature overnight. Next, the reaction mixture was warmed to 70° C. for 1 h when LCMS showed desired product. The reaction was quenched with 1N HCl. The reaction mixture was extracted three times with EtOAc. Purification on silica gel using EtOAc and hexanes permitted the isolation of ethyl 7-((5R,7S)-2-oxo-3-oxa-1-azaspiro[4.4]nonan-7-yl)-4,5-dihydronaphtho[2,1-b]thiophene-2-carboxylate (120 mg, 0.302 mmol, 34% yield); yield of 2 steps. LCMS (M+H): 398.2; LC retention time: 1.01 min (analytical HPLC Method A); $^1$H NMR (400 MHz, CHLOROFORM-d) δ 8.04 (s, 1H), 7.48 (d, J=7.9 Hz, 1H), 7.17-7.06 (m, 2H), 5.44 (br. s., 1H), 4.44-4.35 (m, 3H), 4.35-4.28 (m, 1H), 3.17-3.06 (m, 1H), 3.05-2.97 (m, 4H), 2.38 (dd, J=13.3, 7.4 Hz, 1H), 2.26-2.10 (m, 2H), 2.05-1.93 (m, 2H), 1.93-1.81 (m, 1H), 1.42 (t, J=7.2 Hz, 3H).

Intermediate 21C: (5R,7S)-7-(2-(hydroxymethyl)-4,5-dihydronaphtho[2,1-b]thiophen-7-yl)-3-oxa-1-azaspiro[4.4]nonan-2-one

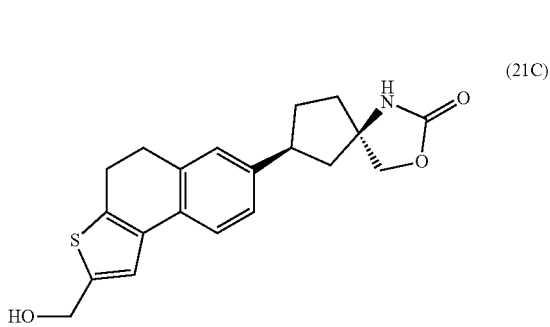 [SMILES: O=C1N[C@@]2(CC[C@H](c3ccc4c(c3)CCc3sc(CO)cc3-4)C2)CO1]

(21C)

To a solution of ethyl 7-((5R,7S)-2-oxo-3-oxa-1-azaspiro[4.4]nonan-7-yl)-4,5-dihydronaphtho[2,1-b]thiophene-2-carboxylate (120 mg, 0.3 mmol) in THF (3 mL) was added LiBH$_4$ (2 M, 755 µL, 1.509 mmol). After the gas evolution had ceased, the tube was capped and the reaction mixture was warmed heated to 70° C. for 5 h when LCMS showed about 90% conversion. The reaction was quenched with 1 N HCl. The reaction mixture was diluted with EtOAc. The aqueous layer was extracted three times with EtOAc. The organic layers were combined, dried over sodium sulfate, and concentrated under reduced pressure to afford (5R,7S)-7-(2-(hydroxymethyl)-4,5-dihydronaphtho[2,1-b]thiophen-7-yl)-3-oxa-1-azaspiro[4.4]nonan-2-one (100 mg, 0.28 mmol, 93% yield) as a white solid. LCMS (M+H—H$_2$O): 338.1; LC retention time: 0.82 min (analytical HPLC Method A).

Intermediate 21D: 7-((5R,7S)-2-oxo-3-oxa-1-azaspiro[4.4]nonan-7-yl)-4,5-dihydronaphtho[2,1-b]thiophene-2-carbaldehyde

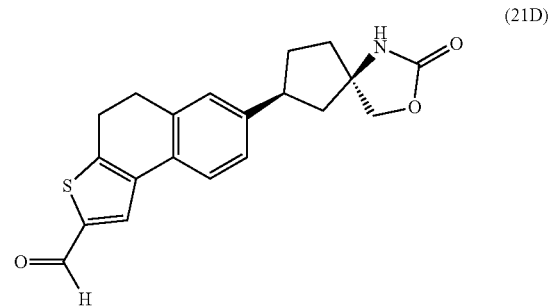 [SMILES: O=Cc1cc2c(s1)CCc1cc([C@H]3CC[C@]4(COC(=O)N4)C3)ccc1-2]

(21D)

To a solution of (5R,7S)-7-(2-(hydroxymethyl)-4,5-dihydronaphtho[2,1-b]thiophen-7-yl)-3-oxa-1-azaspiro[4.4]nonan-2-one (36 mg, 0.1 mmol) in DCM (2 mL) were added sequentially Hunig's base (87 µL, 0.5 mmol), DMSO (71 µL, 1 mmol) and SO$_3$-pyridine (64 mg, 0.4 mmol) at 0° C. The reaction was followed by LCMS and stalled at a 1:1 ratio of starting material:desired product. The reaction mixture was diluted with DCM and extracted with water followed by 1N HCl. The organic layer was dried and concentrated under reduced pressure to afford a white solid. LCMS (M+H): 354.0; LC retention time: 0.89 min (analytical HPLC Method A).

Intermediate 21E: (5R,7S)-7-(2-(pent-1-en-1-yl)-4,5-dihydronaphtho[2,1-b]thiophen-7-yl)-3-oxa-1-azaspiro[4.4]nonan-2-one

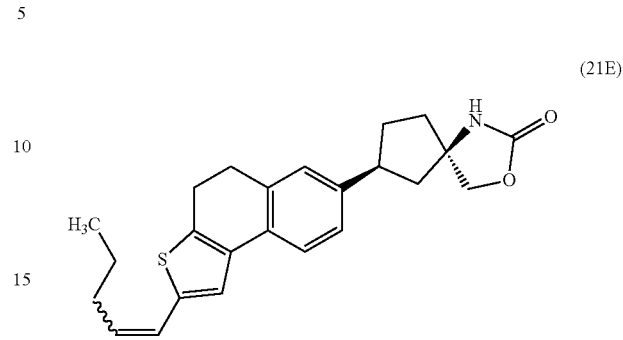

(21E)

To a solution of bromo(butyl)triphenylphosphorane (60 mg, 0.15 mmol) in THF (2 mL) was added LiHMDS (1M, 0.15 mL, 0.15 mmol) at room temperature. The solution was stirred for 30 min and turned yellow. To this solution was added crude 7-((5R,7S)-2-oxo-3-oxa-1-azaspiro[4.4]nonan-7-yl)-4,5-dihydronaphtho[2,1-b]thiophene-2-carbaldehyde (35 mg, 0.1 mmol) in THF (2 mL) and the resulting mixture was stirred for 1 h at room temperature. LCMS showed appearance of the desired product. The reaction mixture was diluted with DCM and washed once with 1N HCl. The organic layer was dried and concentrated under reduced pressure. The corresponding oil was purified by ISCO (gradient 100% hexane to 100% EtOAc) to afford (5R,7S)-7-(2-(pent-1-en-1-yl)-4,5-dihydronaphtho[2,1-b]thiophen-7-yl)-3-oxa-1-azaspiro[4.4]nonan-2-one (3 mg, 7.62 µmol, 8% yield for 2 steps). LCMS (M+H): 394.2; LC retention time: 1.21 min (analytical HPLC Method A).

Intermediate 21F: (5R,7S)-7-(2-pentyl-4,5-dihydronaphtho[2,1-b]thiophen-7-yl)-3-oxa-1-azaspiro[4.4]nonan-2-one

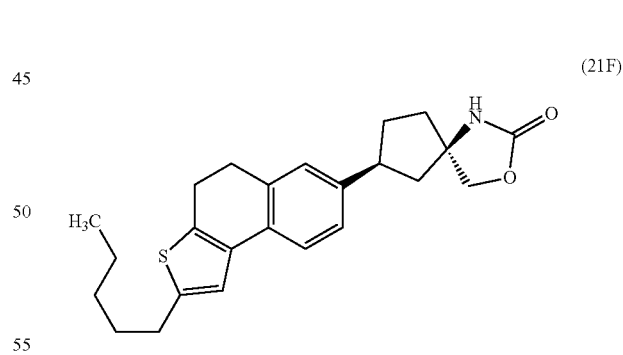

(21F)

To a solution of (5R,7S)-7-(2-(pent-1-en-1-yl)-4,5-dihydronaphtho[2,1-b]thiophen-7-yl)-3-oxa-1-azaspiro[4.4]nonan-2-one (3 mg, 7.6 µmol) in EtOH (0.5 mL) was added Pd—C (1 mg, 7.6 µmol) at room temperature. The reaction mixture was placed under vacuum and backfilled with hydrogen. The reaction was stirred for 1 h when LCMS showed complete conversion. The mixture was filtered over Celite eluting with EtOAc. The solvent was removed under reduced pressure to afford (5R,7S)-7-(2-pentyl-4,5-dihydronaphtho[2,1-b]thiophen-7-yl)-3-oxa-1-azaspiro[4.4]nonan-2-one (2.2 mg, 5.6 µmol, 73% yield) as an oil.

Example 21

To a solution of (5R,7S)-7-(2-pentyl-4,5-dihydronaphtho[2,1-b]thiophen-7-yl)-3-oxa-1-azaspiro[4.4]nonan-2-one (2.2 mg, 5.6 µmol) in dioxane (0.4 mL) was added NaOH (1M, 0.11 mL, 0.11 mmol). The solution was stirred for 2 h at 100° C. when LCMS showed complete conversion. The resulting mixture was concentrated, solubilized in MeOH, and injected on HPLC using Condition B to afford ((1R,3S)-1-amino-3-(2-pentyl-4,5-dihydronaphtho[2,1-b]thiophen-7-yl)cyclopentyl)methanol, TFA (1.5 mg, 3.01 µmol, 54% yield). LCMS (M+H): 370.1; LC retention time: 1.01 min (analytical HPLC Method A); $^1$H NMR (400 MHz, METHANOL-$d_4$) δ 7.44-7.36 (m, 1H), 7.21-7.10 (m, 2H), 7.06 (s, 1H), 3.73-3.57 (m, 2H), 3.16 (td, J=3.4, 1.9 Hz, 1H), 3.03-2.95 (m, 2H), 2.93-2.85 (m, 2H), 2.82 (t, J=7.5 Hz, 2H), 2.50-2.39 (m, 1H), 2.23-2.09 (m, 1H), 2.04-1.90 (m, 3H), 1.84-1.62 (m, 3H), 1.51-1.32 (m, 4H), 1.02-0.87 (m, 3H).

The examples in Table 5 were prepared according to the general procedure described in WO 2011/059784, Example 121.

TABLE 5

| Ex. No. | Structure | MS observed ($M^{+1}$) | HPLC ret. time (min.) | HPLC method |
|---|---|---|---|---|
| 22 | 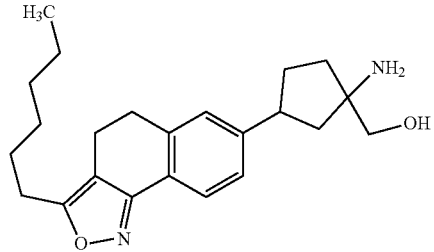 PK1 | 369.2 | 2.57 | C |
| 23 | 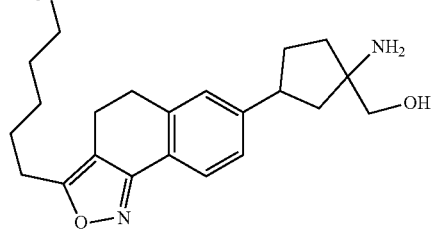 PK2 | 369.2 | 2.57 | C |
| 24 | 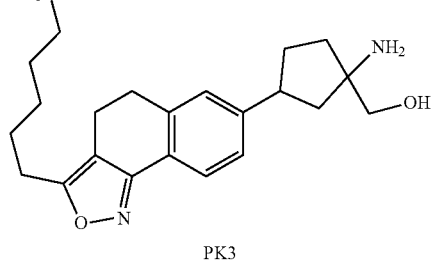 PK3 | 369.2 | 2.57 | C |
| 25 | 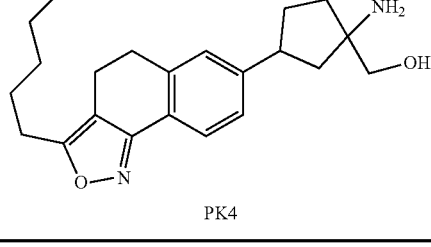 PK4 | 369.2 | 2.57 | C |

Example 26

((1R,3S)-1-amino-3-(2-(2-butoxyethoxy)-4,5-dihydronaphtho[2,1-d]thiazol-7-yl)cyclopentyl)methyl Dihydrogen Phosphate, Trifluoroacetic Acid Salt

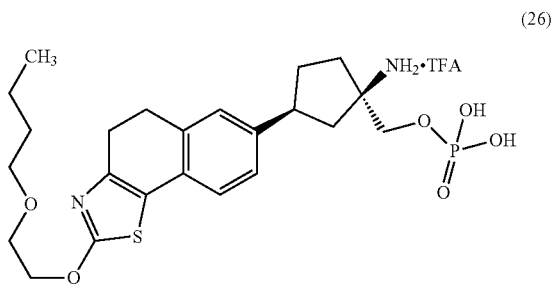

(26)

To a solution of ((1R,3S)-1-amino-3-(2-(2-butoxyethoxy)-4,5-dihydronaphtho[2,1-d]thiazol-7-yl)cyclopentyl)methanol (4 mg, 9.6 µmol) in acetonitrile (0.5 mL) was added pyrophosphoryl chloride (0.013 mL, 0.096 mmol) at 0° C. After 5 min, the cold bath was removed and the reaction mixture was allowed to reach room temperature. The reaction mixture was stirred at this temperature for 1.5 h. LCMS showed complete conversion. The reaction was quenched by the addition of 0.2 mL of water. The reaction mixture was stirred for 15 min and then injected on HPLC using Condition B to afford ((1R,3S)-1-amino-3-(2-(2-butoxyethoxy)-4,5-dihydronaphtho[2,1-d]thiazol-7-yl)cyclopentyl)methyl dihydrogen phosphate, TFA (1.2 mg, 1.9 µmol, 19% yield) as a white solid. LCMS (M+H): 497.2; LC retention time: 0.82 min (analytical HPLC Method A).

The examples in Table 6 were prepared according to the general procedure described in Example 27, by coupling with the appropriate amino alcohol intermediate.

TABLE 6

| Ex. No. | Structure | MS observed ($M^{+1}$) | HPLC ret. time (min.) | HPLC method |
|---|---|---|---|---|
| 27 | 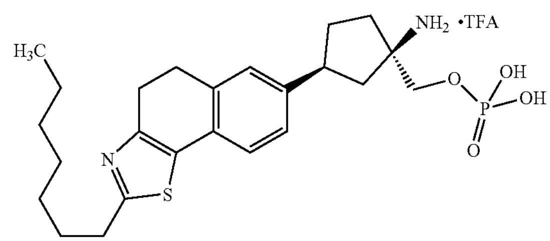 [SMILES: CCCCCCCc1nc2c(s1)-c1ccc([C@H]3CC[C@](N)(COP(=O)(O)O)C3)cc1CC2] | 479.2 | 0.82 | A |
| 28 | 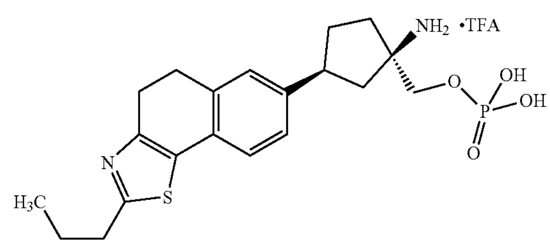 [SMILES: CCCc1nc2c(s1)-c1ccc([C@H]3CC[C@](N)(COP(=O)(O)O)C3)cc1CC2] | 423.2 | 0.67 | A |
| 29 | 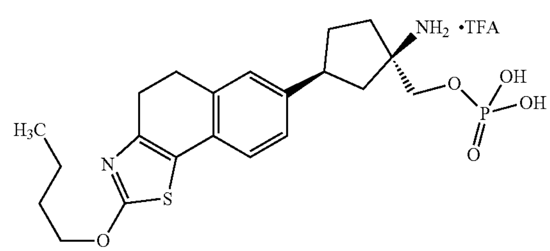 [SMILES: CCCCOc1nc2c(s1)-c1ccc([C@H]3CC[C@](N)(COP(=O)(O)O)C3)cc1CC2] | 453.2 | 0.72 | A |
| 30 | 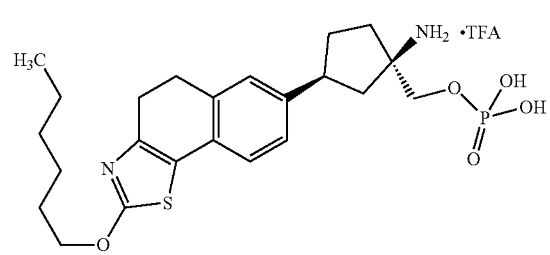 [SMILES: CCCCCCOc1nc2c(s1)-c1ccc([C@H]3CC[C@](N)(COP(=O)(O)O)C3)cc1CC2] | 481.2 | 0.91 | A |

TABLE 6-continued

| Ex. No. | Structure | MS observed (M$^{+1}$) | HPLC ret. time (min.) | HPLC method |
|---|---|---|---|---|
| 31 | 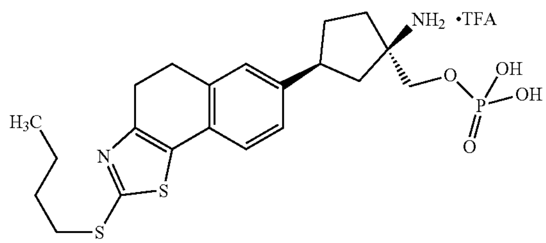 [SMILES: CCCCSc1nc2c(s1)-c1ccc([C@H]3CC[C@](N)(COP(=O)(O)O)C3)cc1CC2] | 469.2 | 0.83 | A |
| 32 | 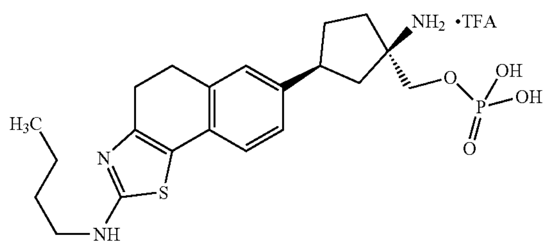 [SMILES: CCCCNc1nc2c(s1)-c1ccc([C@H]3CC[C@](N)(COP(=O)(O)O)C3)cc1CC2] | 452.1 | 0.57 | A |
| 33 | 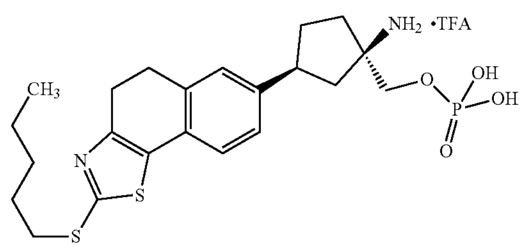 [SMILES: CCCCCSc1nc2c(s1)-c1ccc([C@H]3CC[C@](N)(COP(=O)(O)O)C3)cc1CC2] | 483.2 | 0.88 | A |
| 34 | 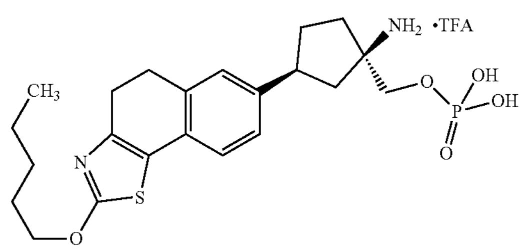 [SMILES: CCCCCOc1nc2c(s1)-c1ccc([C@H]3CC[C@](N)(COP(=O)(O)O)C3)cc1CC2] | 467.2 | 0.85 | A |
| 35 | 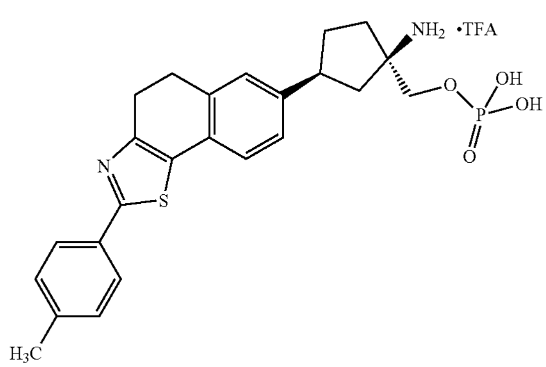 [SMILES: Cc1ccc(-c2nc3c(s2)-c2ccc([C@H]4CC[C@](N)(COP(=O)(O)O)C4)cc2CC3)cc1] | 471.1 | 0.82 | A |

TABLE 6-continued

| Ex. No. | Structure | MS observed ($M^{+1}$) | HPLC ret. time (min.) | HPLC method |
|---|---|---|---|---|
| 36 | 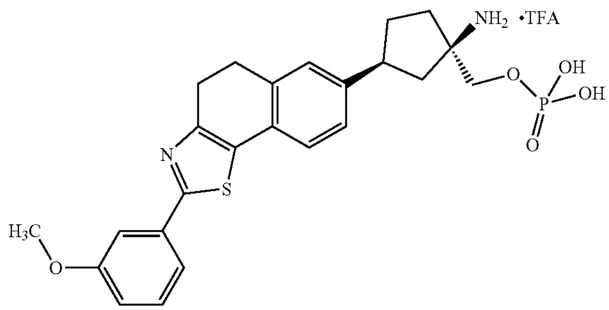 [SMILES: COc1cccc(-c2nc3c(s2)-c2ccc([C@H]4CC[C@](N)(COP(=O)(O)O)C4)cc2CC3)c1] | 487.2 | 0.77 | A |
| 37 | 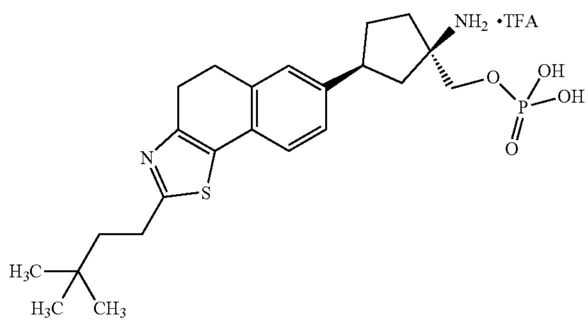 [SMILES: CC(C)(C)CCc1nc2c(s1)-c1ccc([C@H]3CC[C@](N)(COP(=O)(O)O)C3)cc1CC2] | 465.2 | 0.81 | A |
| 38 | 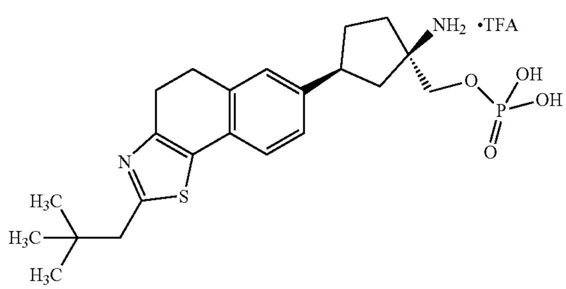 [SMILES: CC(C)(C)Cc1nc2c(s1)-c1ccc([C@H]3CC[C@](N)(COP(=O)(O)O)C3)cc1CC2] | 451.3 | 0.74 | A |
| 39 | 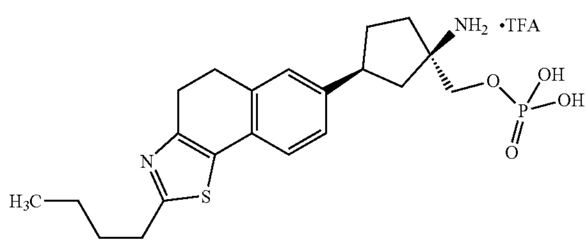 [SMILES: CCCCc1nc2c(s1)-c1ccc([C@H]3CC[C@](N)(COP(=O)(O)O)C3)cc1CC2] | 437.2 | 0.73 | A |
| 40 | 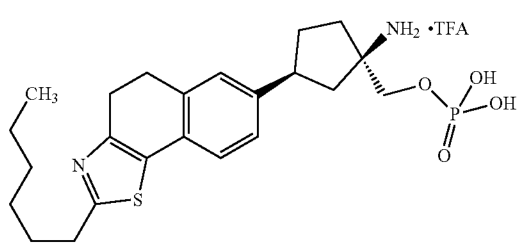 [SMILES: CCCCCCc1nc2c(s1)-c1ccc([C@H]3CC[C@](N)(COP(=O)(O)O)C3)cc1CC2] | 465.3 | 0.82 | A |

TABLE 6-continued

| Ex. No. | Structure | MS observed (M$^{+1}$) | HPLC ret. time (min.) | HPLC method |
|---|---|---|---|---|
| 41 | 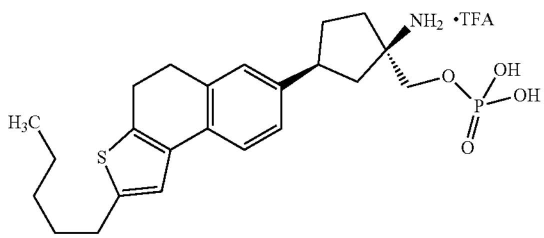 [SMILES: CCCCCc1cc2c(s1)CCc1cc([C@H]3CC[C@](N)(COP(=O)(O)O)C3)ccc1-2] | 450.4 | 0.95 | A |
| 42 | PK1 | 449.3 | 2.63 | C |
| 43 | PK2 | 449.3 | 2.63 | C |
| 44 | PK3 | 449.3 | 2.63 | C |
| 45 | 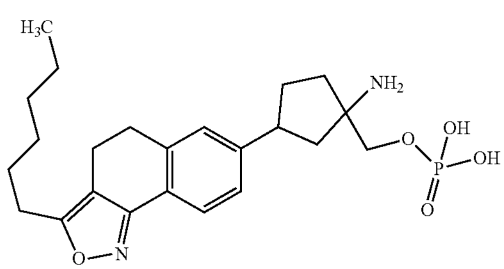 [SMILES: CCCCCCc1onc2c1CCc1cc(C3CCC(N)(COP(=O)(O)O)C3)ccc1-2] | 449.3 | 2.63 | C |

TABLE 6-continued

| Ex. No. | Structure | MS observed ($M^{+1}$) | HPLC ret. time (min.) | HPLC method |
|---|---|---|---|---|
| 46 | 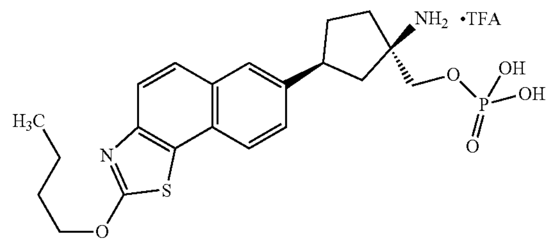 | 452.3 | 0.84 | A |
| 47 | 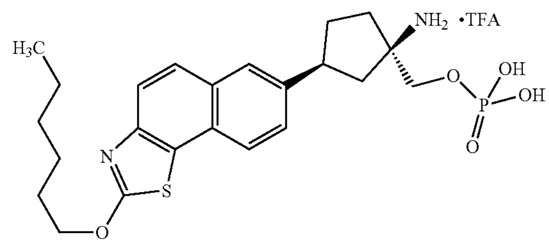 [SMILES: CCCCCCOc1nc2ccc3cc([C@H]4CC[C@](N)(COP(=O)(O)O)C4)ccc3c2s1] | 479.3 | 0.90 | A |
| 48 | 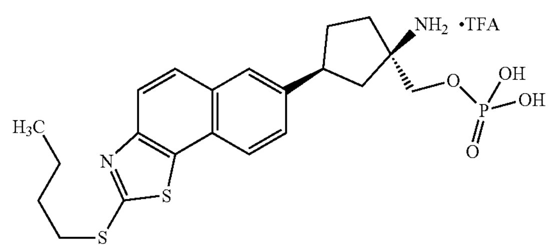 [SMILES: CCCCSc1nc2ccc3cc([C@H]4CC[C@](N)(COP(=O)(O)O)C4)ccc3c2s1] | 467.3 | 0.86 | A |

Examples 49 and 50

(3-amino-3-(hydroxymethyl)pyrrolidin-1-yl)(2-(3-phenyl-4-(trifluoromethyl)isoxazol-5-yl)-4,5-dihydronaphtho[2,1-d]thiazol-7-yl)methanone (49 and 50)

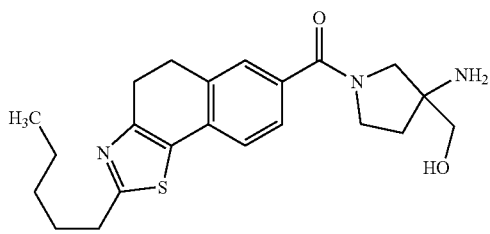

Preparation 49A: 2-pentyl-4,5-dihydronaphtho[2,1-d]thiazole-7-carboxylic Acid (49A)

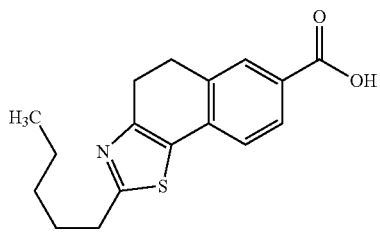

7-Iodo-2-pentyl-4,5-dihydronaphtho[2,1-d]thiazole (PCT Int. Appl. (2011), WO 2011059784 A1 2011051) (100 mg, 0.261 mmol) was dissolved in anhydrous tetrahydrofuran (5 ml). The solution was cooled to approximately −20° C. (ethylene glycol/dry ice—the bath was at −30° C.). Isopropylmagnesium chloride (0.248 ml, 0.496 mmol) was added dropwise. The reaction mixture was allowed to warm to room temperature and stir for 1 hour before dry $CO_2$ gas was bubbled through the reaction solution. The mixture stirred at room temperature for 1 hour at which time LC-MS analysis indicated that the reaction was complete. The reaction was quenched the reaction with 1N HCl. The reaction mixture was stirred at room temperature for 1 h. The solvent was evaporated. The resulting residue was sonicated in 4 ml acetonitrile, resulting in the formation of the Preparation 49A as a white solid (48 mg, yield 59%). HPLC Ret time=3.93 min (condition K); LC/MS $M^{+1}$=302.1.

Examples 49 and 50

To a reaction flask were added 2-pentyl-4,5-dihydronaphtho[2,1-d]thiazole-7-carboxylic acid (46 mg, 0.153 mmol), (3-aminopyrrolidin-3-yl)methanol, 2 HCl (31.7 mg, 0.168 mmol), ethyl acetate (2 mL) and DMF (0.500 mL). The mixture was sonicated for 10 mins before 1-propanephosphonic acid cyclic anhydride (50% in ethyl acetate) (0.109 mL, 0.183 mmol) was added dropwise. The mixture was stirred for 5 mins before DIPEA (0.107 mL, 0.610 mmol) was added. The mixture was stirred at room temperature for 2 hours, at which time LC-MS showed completed conversion. The reaction was quenched (3 mL of 1N HCl). The mixture was stirred for 40 minutes. The resulting material was purified on reverse phase HPLC to afford 55 mg of racemic product. The racemic material was separated by chiral separation.

Preparative Chromatographic Conditions: Instrument: Berger SFC MGII Column: Chiral AS-H 25×3 cm ID, 5 μm; Flow rate: 85.0 mL/min; Mobile Phase: 75/25 $CO_2$/MeOH w/0.1% DEA; Detector Wavelength: 220 nm; Sample Prep and Inj. Volume: 3000 μL of 55 mg dissolved in 15 mL 2:1 MeOH:ACN. Analytical Chromatographic Conditions: Instrument: Berger analytical SFC (LVL-L4021 Lab); Column: Chiral AS-H 250×4.6 mm ID, 5 μm; Flow rate: 2.0 mL/min; Mobile Phase: 75/25 $CO_2$/MeOH w/0.1% DEA.

Example 49: PK1 (13 mg): HPLC Ret. Time: 0.77 min (condition G), LC/MS $M^{+1}$=400. $^1$H NMR (400 MHz, METHANOL-$d_4$) δ 7.49-7.36 (m, 2H), 7.34-7.29 (m, 1H), 3.88-3.68 (m, 2H), 3.66-3.44 (m, 3H), 3.17-3.07 (m, 2H), 3.05-2.94 (m, 4H), 1.95-1.72 (m, 4H), 1.48-1.36 (m, 5H), 1.00-0.88 (m, 3H).

Example 50: PK2 (11 mg): HPLC Ret. Time: 0.77 min (condition G), LC/MS $M^{+1}$=400.1. $^1$H NMR (400 MHz, METHANOL-$d_4$) δ 7.51-7.36 (m, 2H), 7.35-7.30 (m, 1H), 3.87-3.71 (m, 2H), 3.71-3.52 (m, 3H), 3.17-3.07 (m, 2H), 3.07-2.96 (m, 4H), 2.04 (br s, 1H), 1.91-1.72 (m, 3H), 1.50-1.29 (m, 5H), 1.03-0.88 (m, 3H).

Example 51

(3-amino-3-(hydroxymethyl)pyrrolidin-1-yl)(2-(3-phenyl-4-(trifluoromethyl)isoxazol-5-yl)-4,5-dihydronaphtho[2,1-d]thiazol-7-yl)methanone

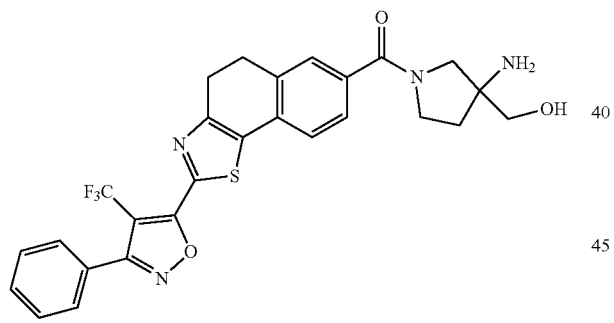

(51)

Preparation 51A: 2-(3-phenyl-4-(trifluoromethyl)isoxazol-5-yl)-4,5-dihydronaphtho[2,1-d]thiazole-7-carbaldehyde

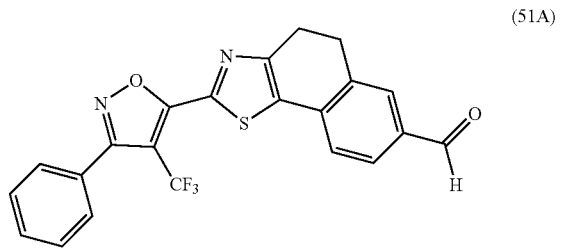 [SMILES: O=Cc1ccc2c(c1)CCc1nc(-c3onc(-c4ccccc4)c3C(F)(F)F)sc1-2]

(51A)

To a clear solution of 3-phenyl-4-(trifluoromethyl)-5-(7-vinyl-4,5-dihydronaphtho[2,1-d]thiazol-2-yl)isoxazole (ref. *J. Med. Chem.* 2016, 59 (21), 9837-9854) (520 mg, 1.225 mmol) in THF (15 ml) were sequentially added NMO in water (0.635 mL, 3.06 mmol) and osmium tetroxide in water (0.449 mL, 0.074 mmol) at room temperature. The mixture was stirred at room temperature overnight. Sodium periodate (655 mg, 3.06 mmol) in $H_2O$ (4 mL) was added to the reaction mixture. The mixture was stirred at room temperature under nitrogen for 2 hours, at which time LC-MS showed reaction was completed. Water (4 mL) was added and a white solid was obtained. The solid material was filtered, washed with water (2×1 mL) and dried under vacuum to afford the titled compound (450 mg, 0.95 mmol, yield 78%). HPLC Ret time=4.29 min (condition K). LC/MS $M^{+1}$=427.1.

Preparation 51B: 2-(3-phenyl-4-(trifluoromethyl)isoxazol-5-yl)-4,5-dihydronaphtho[2,1-d]thiazole-7-carboxylic Acid

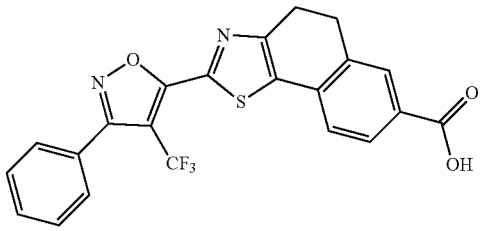

(51B)

To a solution of 2-(3-phenyl-4-(trifluoromethyl)isoxazol-5-yl)-4,5-dihydronaphtho[2,1-d]thiazole-7-carbaldehyde (15 mg, 0.035 mmol) in DMSO (1 ml), was added sodium dihydrogen phosphate (10.97 mg, 0.091 mmol) in 0.3 ml of $H_2O$. The mixture was cooled to 0° C. and sodium chlorite (9.94 mg, 0.088 mmol) in 0.4 ml of $H_2O$ was added slowly. The mixture was allowed to warm to room temperature and then stirred at room temperature for 4 hours. LC-MS analysis showed partial conversion. An additional 2 eq. of sodium chlorite was added and the mixture was stirred at room temperature for 15 hours and then heated to 50° C. for 45 mins, at which time LC-MS analysis showed the reaction to be complete. The mixture was poured into cold 1N HCl (15 mL), stirred, and then extracted with EtOAc. The organic layer was concentrated and dried under high vacuum overnight to afford Preparation 51B (10 mg, 0.023 mmol, yield 64%). HPLC Ret time=4.07 min (condition K); LC/MS $M^{+1}$=443.2.

Preparation 51C: 3-((tert-butoxycarbonyl)amino)-1-(2-(3-phenyl-4-(trifluoromethyl) isoxazol-5-yl)-4,5-dihydronaphtho[2,1-d]thiazole-7-carbonyl)pyrrolidine-3-carboxylic Acid (51C)

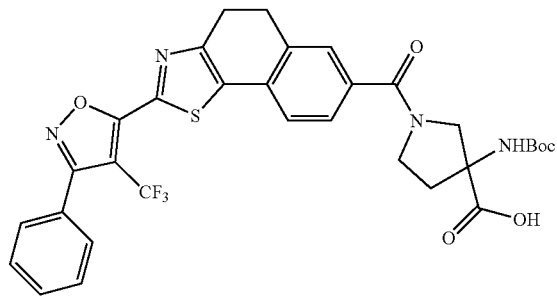

2-(3-phenyl-4-(trifluoromethyl)isoxazol-5-yl)-4,5-dihydronaphtho[2,1-d]thiazole-7-carboxylic acid (50 mg, 0.113 mmol) was dissolved into DMF (0.3 mL) and CH$_2$Cl$_2$ (1.5 mL) cosolvent. To this solution were added N1-((ethylimino)methylene)-N3,N3-dimethylpropane-1,3-diamine hydrochloride (22.75 mg, 0.119 mmol) and HOBT (18.17 mg, 0.119 mmol). The mixture was stirred at room temperature for 50 min. Next, 3-((tert-butoxycarbonyl)amino)pyrrolidine-3-carboxylic acid (26.0 mg, 0.113 mmol) was added. The mixture was stirred at room temperature overnight at which time LC-MS analysis showed the reaction to be complete. The mixture was poured into 40 ml CH$_2$Cl$_2$ and washed twice with 0.5 N HCl. The organic layer was dried over Na$_2$SO$_4$ and concentrated under vacuum to afford Preparation 51C (60 mg, 0.09 mmol, 81%). HPLC Ret. Time=1.06 min (condition G); LC/MS M$^{+1}$=655.2.

Preparation 51D: Methyl 3-amino-1-(2-(3-phenyl-4-(trifluoromethyl)isoxazol-5-yl)-4,5-dihydronaphtho[2,1-d]thiazole-7-carbonyl)pyrrolidine-3-carboxylate (51D)

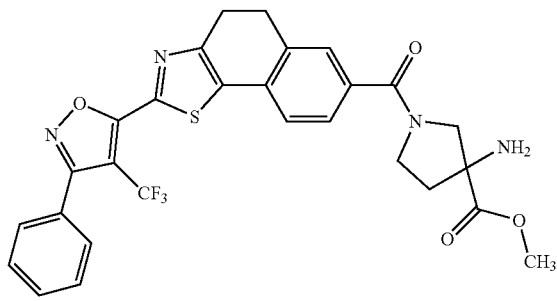

Into CH$_2$Cl$_2$ (3 mL) was dissolved 3-((tert-butoxycarbonyl)amino)-1-(2-(3-phenyl-4-(trifluoromethyl)isoxazol-5-yl)-4,5-dihydronaphtho[2,1-d]thiazole-7-carbonyl) pyrrolidine-3-carboxylic acid (60 mg, 0.092 mmol). The solution was cooled to 0° C. with an ice water bath before oxalyl dichloride (8.79 µl, 0.101 mmol) was added, followed by the addition of 2 drops of DMF. The mixture was stirred at 0° C. for 5 mins. Next, CH$_2$Cl$_2$ was evaporated by air flow and 3 ml of MeOH was added. The mixture was stirred at room temperature for 4 hours at which time LC-MS analysis showed the desired product peak. The MeOH was removed under vacuum and saturated aqueous NaHCO$_3$ (3 mL) was added. The mixture was extracted with ethyl acetate. The organic layer was dried under high vacuum overnight to provide 55 mg of product (88% yield). HPLC Ret. Time=0.87 min (condition G); LC/MS M$^{+1}$=569.2.

Example 51

To a solution of methyl 3-amino-1-(2-(3-phenyl-4-(trifluoromethyl)isoxazol-5-yl)-4,5-dihydronaphtho[2,1-d]thiazole-7-carbonyl)pyrrolidine-3-carboxylate (55 mg, 0.097 mmol) in MeOH (3 mL) at 0° C. was added NaBH$_4$ (18.30 mg, 0.484 mmol). The mixture was stirred at 0° C. for 2 hours at which time LC-MS analysis showed the reaction to be complete. The reaction was quenched with 1 N HCl and purified on reverse phase HPLC. The product containing fractions were collected and dried under high vacuum overnight to provide 29 mg of product as a racemic mixture. HPLC Ret. Time: 3.43 min (condition K), LC/MS M$^{+1}$=541.2. $^1$H NMR (400 MHz, METHANOL-d$_4$) δ 7.73-7.44 (m, 8H), 3.87-3.69 (m, 6H), 3.22 (s, 4H), 2.27 (s, 1H), 2.16 (s, 1H).

Examples 52 and 53

The racemic mixture of Example 51 (approximately 35 mg) was separated by chiral separation. The fractions ("PK-1" and "PK-2") were collected in MeOH with 0.1% diethylamine. The purity of each fraction is estimated to be >98% based on the preparative chromatogram.

Preparative Chromatographic Conditions: Instrument: Berger SFC MGII (LVL-L4021 Lab); Column: AS-H 50×3 cm ID, 5 µm; Flow rate: 85.0 mL/min; Mobile Phase: 85/15 CO$_2$/MeOH (with 0.1% DEA); Detector Wavelength: 220 nm.

Example 52: PK1: HPLC Ret time=3.14 min (condition K); LC/MS M$^{+1}$=541.2. $^1$H NMR (400 MHz, METHANOL-d$_4$) δ 7.72-7.52 (m, 8H), 3.94-3.79 (m, 5H), 3.72 (br. s., 1H), 3.28-3.22 (m, 4H), 2.38-2.27 (m, 1H), 2.19 (br. s., 1H).

Example 53: PK2: HPLC Ret time=3.08 min (condition K); LC/MS M$^{+1}$=541.2. $^1$H NMR (400 MHz, METHANOL-d$_4$) δ 7.73-7.49 (m, 8H), 3.92-3.74 (m, 3H), 3.72-3.64 (m, 2H), 3.62 (s, 1H), 3.25 (s, 4H), 2.17-2.02 (m, 1H), 1.87 (d, J=13.0 Hz, 1H).

Biological Assays

The compounds of Formula (I), Formula (II), Formula (III), and Formula (IV), and salts thereof in which R$_2$ is —OH, engage their biological targets (e.g. S1P1) after bioactivation through phosphorylation of the alcohol to provide an active phosphate ester compound of Formula (I), Formula (II), Formula (III), and Formula (IV), or salts thereof, in which R$_2$ is —OP(O)(OH)$_2$. In vitro characterization of biological activity of the examples was conducted on synthetically prepared samples of the phosphorylated compounds.

Receptor [$^{35}$S] GTPyS Binding Assays: (S1P1 GTPyS/S1P3 GTPyS)

Compounds were loaded in a 384 Falcon v-bottom plate (0.5 µl/well in a 11 point, 3-fold dilution). Membranes prepared from S1Pi/CHO cells or EDG3-Ga15-bla HEK293T cells (EDG3 equivalent S1P3) were added to the compound plate (40 µl/well, final protein 3 µg/well) with MULTIDROP®. [$^{35}$S] GTP (1250 Ci/mmol, Perkin Elmer)

was diluted in assay buffer: 20 mM HEPES, pH7.5, 10 mM MgCl$_2$, 150 mM NaCl, 1 mM EGTA (ethylene glycol tetraacetic acid), 1 mM DTT (Dithiothreitol), 10 μM GDP, 0.1% fatty acid free BSA, and 10 μg/ml Saponin to 0.4 nM. 40 μl of the [$^{35}$S] GTP solution was added to the compound plate with a final concentration of 0.2 nM. The reaction mixture was kept at room temperature for 45 min. At the end of incubation, all the mixtures in the compound plate were transferred to Millipore 384-well FB filter plates via the VELOCITY 11® Vprep liquid handler. The filter plate was washed with water 4 times by using the manifold Embla plate washer and dried at 60° C. for 45 min. MicroScint 20 scintillation fluid (30 μl) was added to each well for counting on the Packard TOPCOUNT®. EC$_{50}$ is defined as the agonist concentration that corresponds to 50% of the Ymax (maximal response) obtained for each individual compound tested.

A smaller value for GTPyS S1 P1 EC$_{50}$ value indicated greater activity for the compound in the GTPyS S1P1 binding assay. A larger value for the GTPyS S1 P3 EC$_{50}$ value indicated less activity in the GTPyS S1 P3 binding assay (Table A).

TABLE A

| Ex. No. | S1P1 GTPgS (EC$_{50}$, nM) | S1P1 GTPgS (Ymax) | S1P3 GTPgS (EC$_{50}$, nM) |
| --- | --- | --- | --- |
| 26 | 1 | 107% | 190 |
| 27 | 10 | 98% | >3000 |
| 28 | 19 | 79% | >3000 |
| 29 | 30 | 58% | >3000 |
| 30 | 12 | 102% | >3000 |
| 31 | 20 | 58% | >3000 |
| 32 | 133 | 49% | >3000 |

Blood Lymphocyte Reduction (BLR) Assay in Rodent:

Lewis rats were dosed orally with vehicle alone (polyethylene glycol 300, "PEG300") or with test compounds. Compounds were dosed as a solution or suspension in the vehicle, adjusted to reflect the free amount of test article in the event that salt forms are utilized. Blood was drawn at 24 hr and blood lymphocyte counts were determined on an ADVIA 120 Hematology Analyzer (Siemens Healthcare Diagnostics). The results were measured as a reduction in the percentage of circulating lymphocytes as compared to the vehicle treated group at the time of measurement. The results represent the average results of all animals within each treatment group (n=2). The results of the Blood Lymphocyte Reduction assay (BLR) in rat described hereinabove are shown in Table B.

TABLE B

| | 4 Hours | | | | 24 Hours | | | |
| --- | --- | --- | --- | --- | --- | --- | --- | --- |
| Ex. No. | BL ($\times 10^3$/mm$^3$) | Lymp. Red. | Patent (nM) | Phos. (nM) | BL ($\times 10^3$/mm$^3$) | Lymp. Red. | Patent (nM) | Phos. (nM) |
| 1 | 5.7 | 40% | 66 | 63 | 1.8 | 77% | 111 | 303 |
| 2 | 4.9 | 41% | 108 | 79 | 8.2 | 0% | <19 | <10 |
| 5 | 2.8 | 66% | 77 | 97 | 4.5 | 48% | 9 | 8 |
| 6 | 3.4 | 59% | 109 | 142 | 1.5 | 82% | 66 | 164 |
| 7 | 1.9 | 79% | 1 | 120 | 1.2 | 87% | 142 | 58 |
| 8 | 2.5 | 74% | 35 | 34 | 2.4 | 68% | 7 | 20 |
| 9 | 2.8 | 66% | 72 | 62 | 1.4 | 82% | 31 | <5 |
| 10 | 1.7 | 82% | 9 | 15 | 4.1 | 48% | 1 | 2 |
| 11 | 2.3 | 72% | 87 | 43 | 2.1 | 76% | 16 | 10 |
| 12 | 2.8 | 67% | 81 | 71 | 1.8 | 80% | 29 | 26 |
| 13 | 2.5 | 73% | 65 | 33 | 1.4 | 83% | 78 | 249 |
| 14 | 2.6 | 69% | 15 | 10 | 2.1 | 75% | 8 | 8 |
| 15 | 1.7 | 80% | 31 | | 1.8 | 80% | 17 | |
| 16 | 2.9 | 65% | 28 | 5 | 1.9 | 77% | 21 | <5 |
| 17 | 5.8 | 37% | 33 | 569 | 8.4 | 0% | 0 | 192 |
| 18 | 5.9 | 30% | 113 | | 6.4 | 27% | 18 | |
| 19 | 7.5 | 9% | 48 | 12 | 8.2 | 2% | 37 | 19 |
| 20 | 5.7 | 31% | 97 | 39 | 3.1 | 63% | 68 | <5 |

The compounds of the present invention possess activity as agonists of the S1P1 receptor, leading to the reduction of circulating blood lymphocytes, and thus may be used in treating, preventing, or curing various S1 P1 receptor-related conditions. The surprising selectivity of the compounds of the present invention indicate their potential use in treating, preventing, or curing autoimmune and inflammatory diseases such as multiple sclerosis, rheumatoid arthritis, inflammatory bowel diseases, lupus, psoriasis, or vascular diseases. Other potential uses of the compounds of the present invention include minimizing or reducing rejection of transplanted organs.

What is claimed is:

1. A compound of Formula (II):

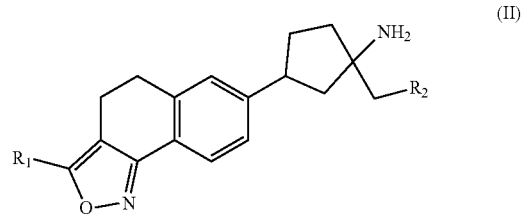

or a salt thereof, wherein:

R$_1$ is —(CH$_2$)$_5$CH$_3$ or

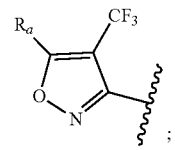

$R_a$ is —$(CH_2)_5CH_3$; and
$R_2$ is —OH or —$OP(O)(OH)_2$.

2. The compound according to claim 1 wherein said compound is (1-amino-3-(3-hexyl-4,5-dihydronaphtho[1,2-c]isoxazol-7-yl)cyclopentyl)methyl dihydrogen phosphate (42-45).

3. A compound of Formula (III):

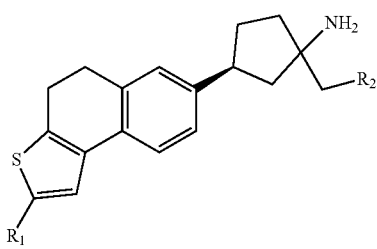

(III)

or a salt thereof, wherein:
$R_1$ is —$(CH_2)_4CH_3$; and
$R_2$ is —OH or —$OP(O)(OH)_2$.

4. A compound of Formula (IV):

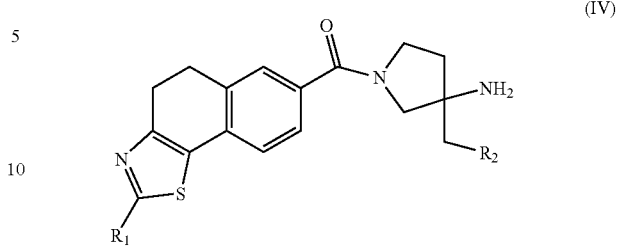

(IV)

or a salt thereof, wherein:
$R_1$ is —$(CH_2)_4CH_3$ or -isoxazolyl substituted with —$CF_3$ and phenyl; and
$R_2$ is —OH or —$OP(O)(OH)_2$.

5. The compound according to claim 4 wherein said compound is (3-amino-3-(hydroxymethyl)pyrrolidin-1-yl)(2-(3-phenyl-4-(trifluoromethyl)isoxazol-5-yl)-4,5-dihydronaphtho[2,1-d]thiazol-7-yl)methanone (49 and 50); or (3-amino-3-(hydroxymethyl)pyrrolidin-1-yl)(2-(3-phenyl-4-(trifluoromethyl)isoxazol-5-yl)-4,5-dihydronaphtho[2,1-d]thiazol-7-yl)methanone (51 to 53).

6. A pharmaceutical composition comprising a compound according to claim 1 or a pharmaceutically-acceptable salt thereof; and a pharmaceutically acceptable carrier.

7. A pharmaceutical composition comprising a compound according to claim 3 or a pharmaceutically-acceptable salt thereof; and a pharmaceutically acceptable carrier.

* * * * *